(12) United States Patent
Meilhac et al.

(10) Patent No.: US 11,583,596 B2
(45) Date of Patent: Feb. 21, 2023

(54) RADIOLABELED DARAPLADIB AND ANALOGS THEREOF AND THEIR USE AS IMAGING COMPOUNDS

(71) Applicants: INSERM (INSTITUT NATIONAL DE LA SANTÉ ET DE LA RECHERCHE MÉDICALE), Paris (FR); UNIVERSITE DE LA REUNION, Saint Denis (FR)

(72) Inventors: Olivier Meilhac, Sainte-Clotilde (FR); Emmanuelle Jestin, Sainte-Clotilde (FR); Florian Guibbal, Sainte-Clotilde (FR); Sébastien Benard, Sainte-Clotilde (FR)

(73) Assignees: INSERM (INSTITUT NATIONAL DE LA SANTE ET DE LA RECHERCHE MEDICALE), Paris (FR); UNIVERSITE DE LA REUNION, Saint Denis (FR)

( * ) Notice: Subject to any disclaimer, the term of this patent is extended or adjusted under 35 U.S.C. 154(b) by 162 days.

(21) Appl. No.: 16/650,532

(22) PCT Filed: Sep. 26, 2018

(86) PCT No.: PCT/EP2018/076163
§ 371 (c)(1),
(2) Date: Mar. 25, 2020

(87) PCT Pub. No.: WO2019/063634
PCT Pub. Date: Apr. 4, 2019

(65) Prior Publication Data
US 2020/0276337 A1    Sep. 3, 2020

(30) Foreign Application Priority Data
Sep. 26, 2017 (EP) .................... 17306272

(51) Int. Cl.
| A61K 49/04 | (2006.01) |
| A61K 51/04 | (2006.01) |
| C07D 239/95 | (2006.01) |
| C07D 403/06 | (2006.01) |
| C07D 405/12 | (2006.01) |
| C07F 5/02 | (2006.01) |
| A61K 9/00 | (2006.01) |

(52) U.S. Cl.
CPC ........ *A61K 51/0459* (2013.01); *C07D 239/95* (2013.01); *C07D 403/06* (2013.01); *C07D 405/12* (2013.01); *C07F 5/025* (2013.01); *A61K 9/0019* (2013.01); *A61K 9/0053* (2013.01)

(58) Field of Classification Search
CPC .............. A61K 51/0459; A61K 9/0053; C07D 239/95; C07D 403/06; C07D 405/12; C07F 5/025
USPC ....................................... 424/9.44
See application file for complete search history.

(56) References Cited

U.S. PATENT DOCUMENTS

2017/0204109 A1* 7/2017 Wan .................... A61P 5/18

FOREIGN PATENT DOCUMENTS

| EP | 1 686 119 A1 | 8/2006 |
| WO | 2015/087239 A1 | 6/2015 |

OTHER PUBLICATIONS

Mossine et al. Org. Lett. 2015, 17, 5780-5783. (Year: 2015).*
Liu et al. J. Med. Chem. 2016, 59, 5115-5120. (Year: 2016).*
Preshlock et al. Chem. Rev. 2016, 116, 719-766. (Year: 2016).*
Guibbal et al.: "Regioselectivity of thiouracil alkylation: Application to optimization of Darapladib synthesis", Bioorganic and Medicinal Chemistry Letters, vol. 28, pp. 787-792, 2018.
Guibbal et al: "Synthesis and Automated Labeling of [18F]Darapladib, a Lp-PLA2 Ligand, as Potential PET Imaging Tool of Atherosclerosis", ACS Medicinal Chemistry Letters, vol. 10, pp. 743-748, 2019.
Zischler et al.: "Alcohol-Enhanced Cu-Mediated Radiofluorination", Chemistry A European Journal, vol. 23, No. 14, pp. 3251-3256, Mar. 8, 2017.

* cited by examiner

*Primary Examiner* — Michael G. Hartley
*Assistant Examiner* — Sean R Donohue
(74) *Attorney, Agent, or Firm* — WCF IP

(57) ABSTRACT

The present inventors have developed new radiolabeled Darapladib and analogs thereof which can be used for the specific detection of vulnerable atherosclerotic plaques by targeting lipoprotein-associated phospholipase A2 (Lp-PLA2) which is a biomarker of choice concerning inflammation and atherosclerosis progression. Thus, the present invention relates to radiolabeled Darapladib and analogs thereof and their use as imaging compounds.

1 Claim, 11 Drawing Sheets

Figure 5
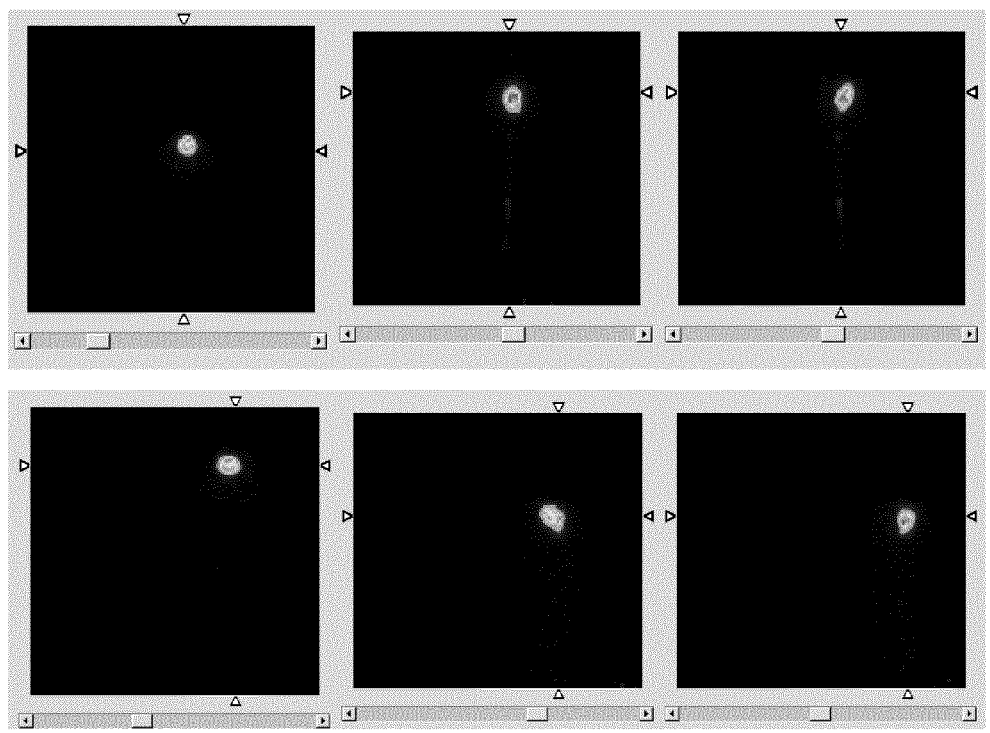
Figure 6A (18F-FDG in C57BL/6)
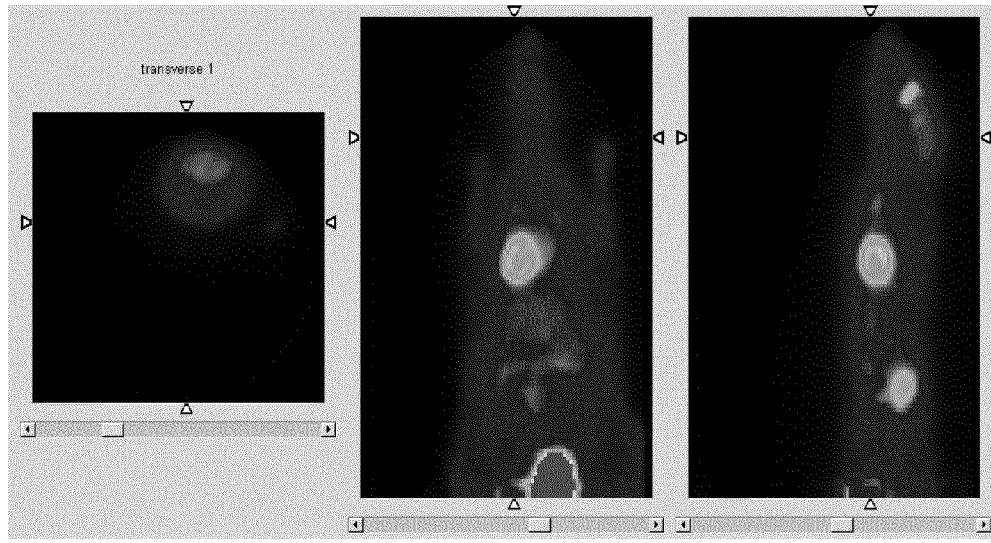

Figure 6B (18F-FDG in ApoE KO)
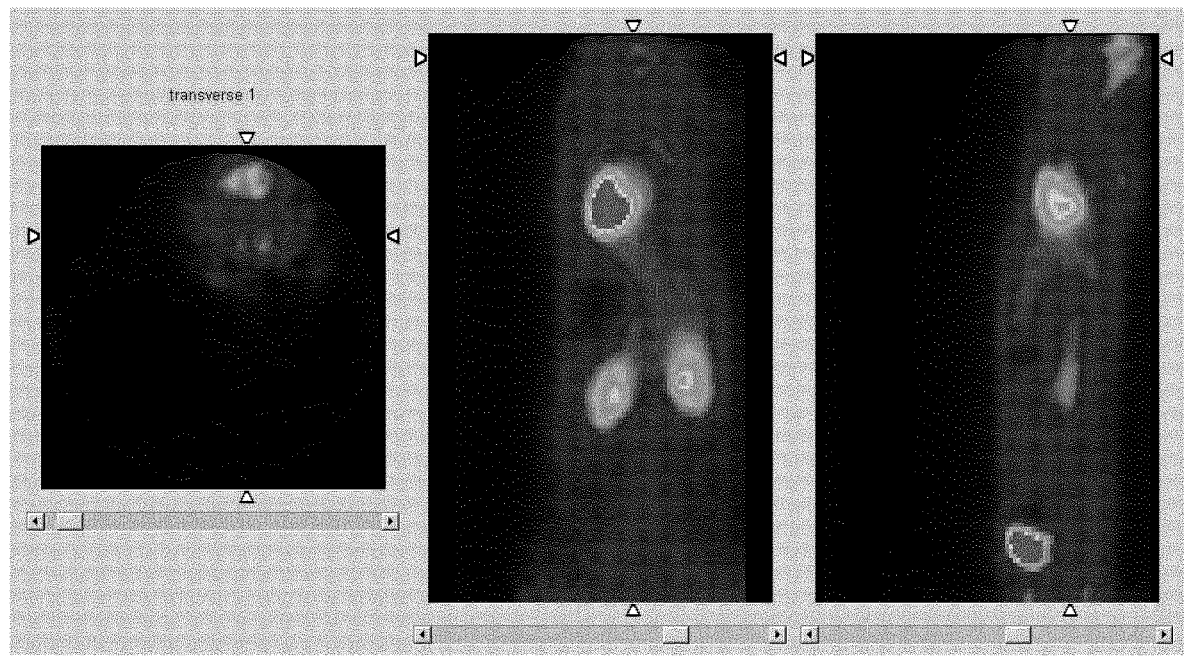
Figure 7A (Aorte 18F-FDG KO ApoE)
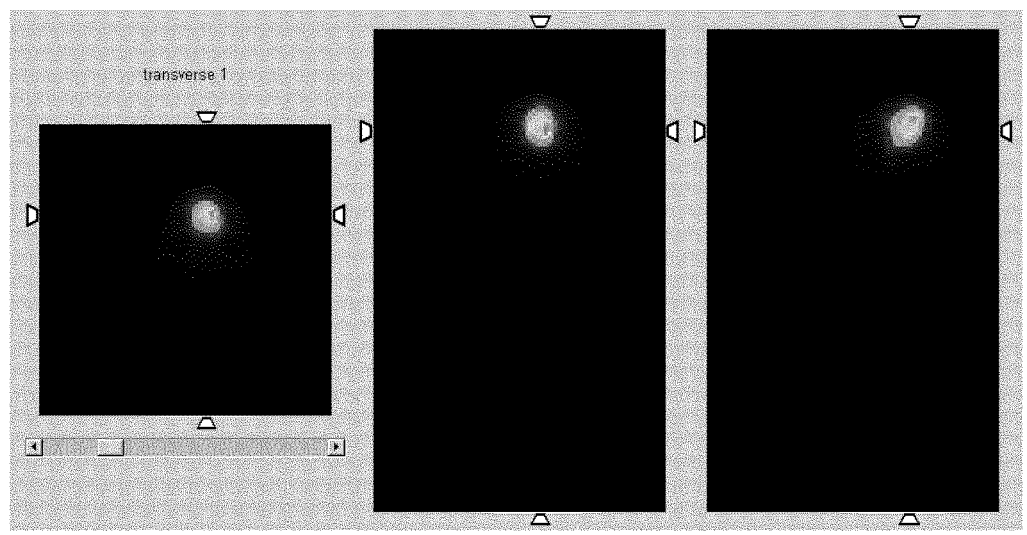

Figure 7B (Aorte 18F-FDG C57BL6)
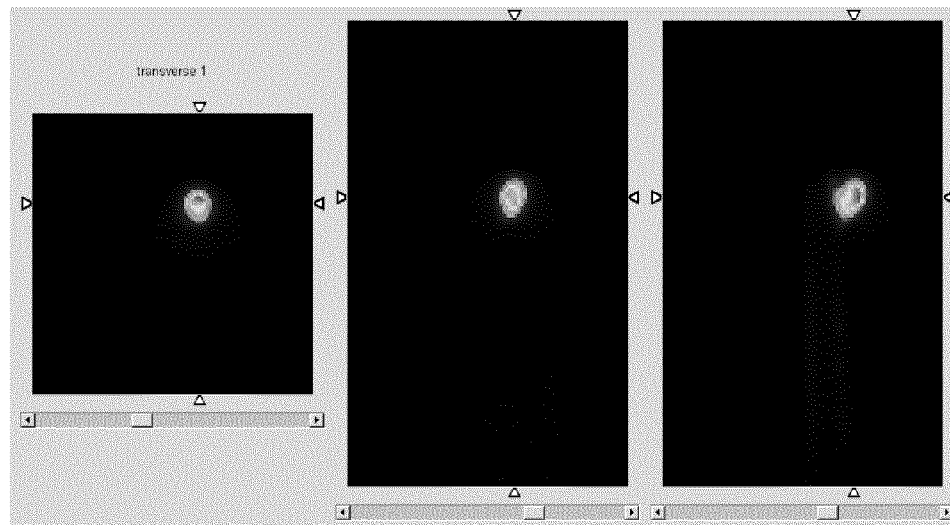
Figure 8
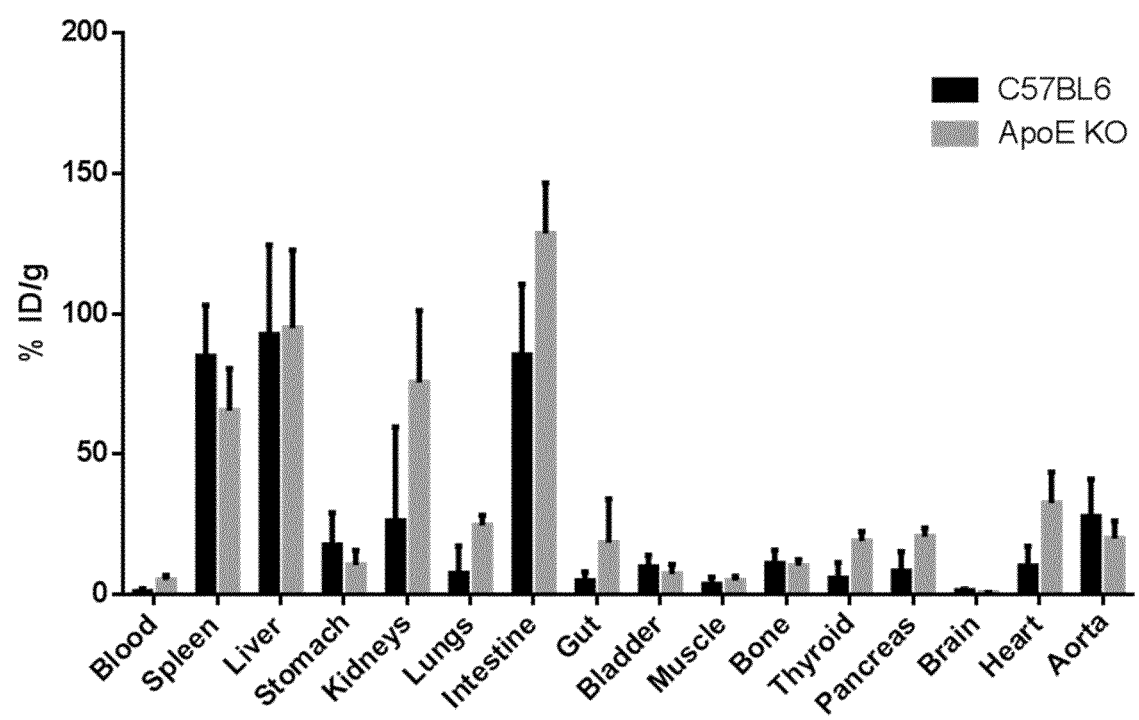

Figure 12A (Aorte KO ApoE with injection of 18F-FDG)
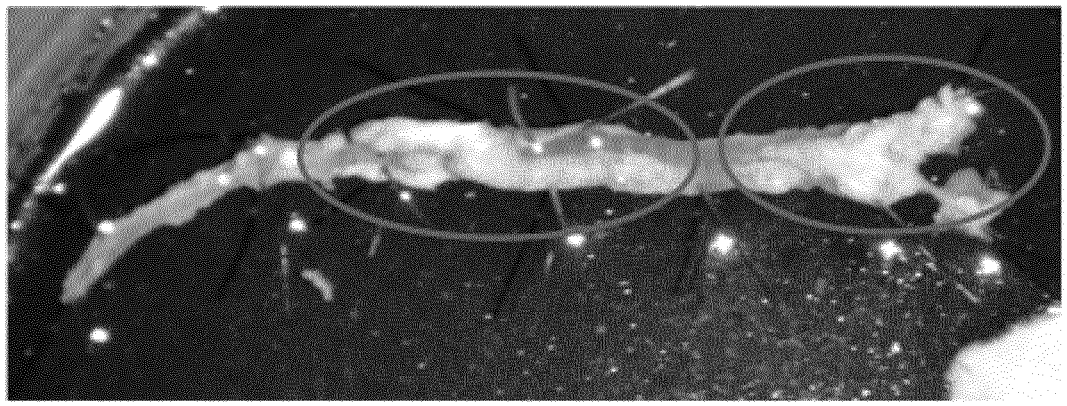
Figure 12B (Aorte KO ApoE with injection of 18F-Darapladib)
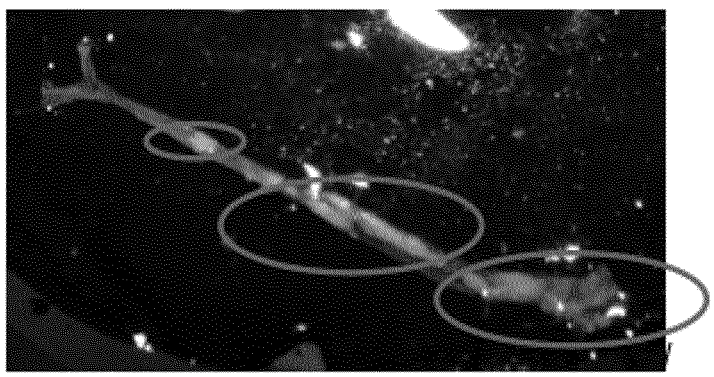
Figure 13A (Aorte C57BL6 with injection of 18F-FDG)
Figure 13B (Aorte C57BL6 with injection of 18F-Darapladib)

**Figure 14A (C57BL/6 after injection of [$^{18}$F]*N1*-FGU herein referred as compound A4)**
**Figure 14B (ApoE after injection of [$^{18}$F]*N1*-FGU herein referred as compound A4)**

Figure 15A (C57BL/6 after injection of [$^{18}$F]*N1*-FGU herein referred as compound A4)
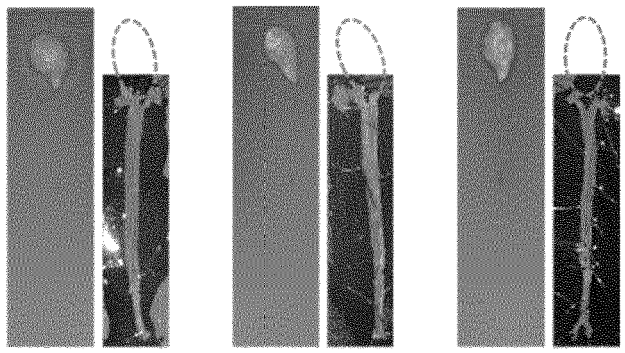
Figure 15B (ApoE after injection of [$^{18}$F]*N1*-FGU herein referred as compound A4)
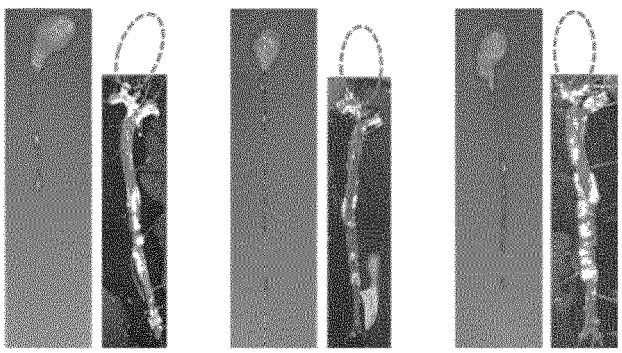
Figure 16A (incubation of human carotid endarterectomy samples with [$^{18}$F]FDG):
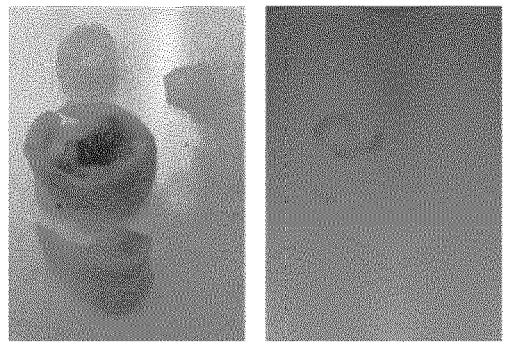

Figure 16B (incubation of human carotid endarterectomy samples with [$^{18}$F]N1-FGU herein referred as compound A4):
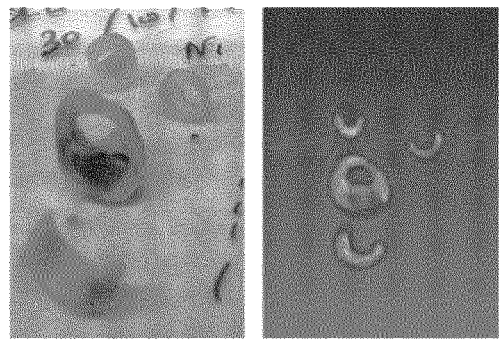
Figure 17A (ApoE KO after injection of $^{18}$F-$O$-FGU herein referred as compound A12):
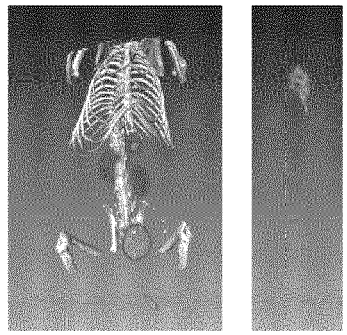
Figure 17B (C57BL/6 after injection of $^{18}$F-$O$-FGU herein referred as compound A12):
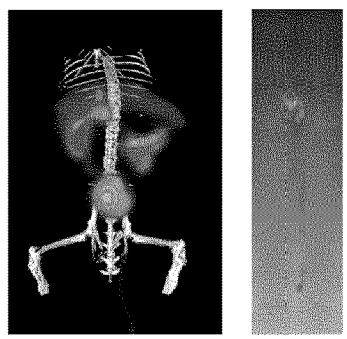

RADIOLABELED DARAPLADIB AND ANALOGS THEREOF AND THEIR USE AS IMAGING COMPOUNDS

INTRODUCTION

The present invention relates to radiolabeled Darapladib and analogs thereof and their use as imaging compounds.

BACKGROUND OF THE INVENTION

Cardiovascular diseases, resulting from coronary and carotid complications, stand for one of the first cause of morbidity and mortality in the world. The concerned subjects show clinical signs when vulnerable atherosclerotic plaques become damaged or cracked. The vulnerable atherosclerotic plaque rupture initiates the formation of a thrombus which clogs vessels, resulting from myocardial ischemia, myocardial infarction or cerebral arteries embolization leading to transient ischemic attack (TIA) or ischemic stroke. Thus, atherosclerotic complications are responsible in western countries for about 50% of death. While progresses have been shown on treating atherosclerotic diseases, fatal events occurrence is still on the rise.

Atherosclerosis is characterized by an accumulation of lipids and leukocytes with the vascular wall of large arteries, leading to their occlusion and subsequent clinical events. Hydrolysis of oxidized phospholipids in low density lipoproteins (LDL) mediated by lipoprotein-associated phospholipase $A_2$ (Lp-$PLA_2$), predominantly produced by activated macrophages, plays an important role in atheroma plaque development by promoting the recruitment of leukocytes. Clinical studies have shown that plasma Lp-$PLA_2$ levels were correlated with cardiovascular events. In situ, the expression of Lp-$PLA_2$ was higher in carotid atherosclerotic plaques from symptomatic than asymptomatic patients.

As previously described, before rupture, vulnerable atherosclerotic plaques are characterized by a high number of inflammatory cells (leukocytes and phagocytic cells) and proteic biomarkers. Thus, by targeting biomarkers associated with vulnerable atherosclerotic plaques, it would be possible to precisely evaluate the inflammatory levels in atheromatous lesions.

Nuclear medicine, by its high sensibility, is able to provide solutions. Labels have been developed in scintigraphy to evaluate the recruitment of macrophages, the production of matrix metalloproteinase, apoptosis, and the increment of phagocytic cells metabolic activity. However, the identification of inflammatory lesions in coronary section remains difficult in particular due to the small size of the plaque, heart and respiratory movement and the absence of specific nuclear label.

Functional molecular imaging can enable diseases tracking at an early step of development or also during drug treatments. Positron Emission Tomography (PET) has become a powerful tool to elucidate disorders ranging from neurological to heart disease. Fluorine-18 is the most widely used radioisotope for PET diagnosis due to its suitable halftime ($t_{1/2}$=109.8 min), high resolution imaging and low perdition of radioligand-target binding. In nuclear medicine, the "gold-standard" for PET diagnosis in many pathologies (cancer, cardiology, neurology etc.) is the Fluorodeoxyglucose or $^{18}$F-FDG. However, this PET label of reference, $^{18}$F-FDG is not suitable to detect vulnerable atherosclerotic plaques in coronary section due to the catch of $^{18}$F-FDG by the myocardium. Furthermore, $^{18}$F-FDG has a poor capture and does not specifically target the atherosclerotic plaques. $^{18}$F-FDG is thus a poor candidate for atherosclerosis diagnosis.

In view of the foregoing, there is a real need of candidates for early diagnosis of vulnerable atheroma plaques that are susceptible to break.

The present invention aims to the early detection of vulnerable atherosclerotic plaques and thus relates to new non-invasive imaging tools to assess plaque vulnerability and localization.

The present inventors have surprisingly found and developed new compounds which can be used for the specific detection of vulnerable atherosclerotic plaques by targeting lipoprotein-associated phospholipase A2 (Lp-$PLA_2$) which is a biomarker of choice concerning inflammation and atherosclerosis progression. Lp-$PLA_2$ is an enzyme produced by inflammatory cells involved in atherogenesis but is especially expressed in necrosis center of atherosclerotic lesions. This enzyme is thus highly present in the fibrous plaque before the complicated lesion phase. Lp-$PLA_2$ rapidly degrades phospholipids present at the surface of oxidized LDL, thus leading to the production of inflammatory and cytotoxic products and consequently to vulnerable plaque rupture. Thus, by targeting the accumulation of inflammatory cells and/or lipoproteins (LDL and/or HDL), the present inventors have found that it was possible to detect diseases associated with Lp-$PLA_2$.

During the last decade, scientists have tried to develop ligands to treat cardiovascular diseases. Darapladib, a new highly potent Lp-$PLA_2$ inhibitor ($IC_{50}$=0.25 nM)[13], was discovered in the early 2000's but failed to reach critical endpoints in phase III clinical trials. The thiouracile ring bearing keto-enol tautomerism has three different alkylation sites that represent a challenge for large scale production.

The present inventors have hypothesized that Darapladib, a potent Lp-$PLA_2$ inhibitor ($IC_{50}$=0.25 nM), could be radiolabeled using $^{18}$F, $^{124}$I and $^{131}$I, and used as ligand rather than a drug, for PET imaging of vulnerable plaques. Thriving on the strong affinity of Darapladib towards Lp-$PLA_2$ and the fluorine already present in the structure, the present inventors decided to use this affinity to target vulnerable atheroma plaques with [$^{18}$F]-Darapladib, [$^{123}$I]-Darapladib [$^{124}$I]-Darapladib, [$^{125}$I]-Darapladib, [$^{131}$I]-Darapladib, and [$^{211}$At]-Darapladib for PET imaging and SPECT (Single-photon emission computed tomography) imaging. They surprisingly found that the original structure of Darapladib could be preserved while having unchanged physico-chemical properties as well as in vivo behavior.

Since Lp-$PLA_2$ inhibitors may be used to thwart the deleterious effect of this enzyme in different pathologies, the present inventors have synthesized their own series of inhibitors using the key structure of Darapladib.

DETAILED DESCRIPTION OF THE PREFERRED EMBODIMENTS

One subject matter of the present invention is a compound of the following general formula (I):

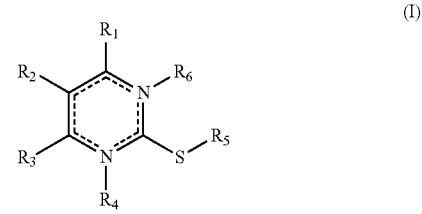

wherein
R$_1$ is =O (i.e. R$_1$ and the carbon atom to which it is attached form a C=O group) or —O—R$_1$', R$_1$' is —(CH$_2$)$_q$—C(=O)—R$_7$ or —(CH$_2$)$_q$—C(=O)—O—R$_8$
wherein R$_8$ represents the following group:

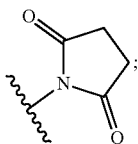 [SMILES: *N1C(=O)CCC1=O]

and
  wherein R$_7$ is —OH; —O—(C$_1$-C$_3$)alkyl group, preferably a methyl or isopropyl group; —N(—R$_{14}$)(—R$_{15}$) wherein
    R$_{14}$ is —H; —(CH$_2$)$_p$—X$_3$; —(CH$_2$)$_p$—C≡CH; —(CH$_2$)$_p$— diethyl-methyl-ammonium; —(CH$_2$)$_p$—N(R$_{16}$)$_2$ wherein R$_{16}$ is (C$_1$-C$_3$)alkyl, preferably an ethyl group;
    R$_{15}$ is selected from —(CH$_2$)$_{p1}$—OH; —(CH$_2$)$_{p1}$—X$_4$; —(CH$_2$)$_{p1}$-Ph-Ph-X$_4$, —(CH$_2$)$_{p1}$-Ph-Ph-(CH$_2$)$_{p2}$—X$_3$; —(CH$_2$)$_{p1}$-Ph-Ph-C≡C—(CH$_2$)$_{p2}$—X$_3$; or —(CH$_2$)$_{p1}$-Ph-Ph-O—(CH$_2$)$_{p2}$—X$_3$, or
    R$_{14}$ and R$_{15}$ form, together with the nitrogen atom to which they are attached, a piperazine, said piperazine being optionally substituted in position 4 with -Ph-O—(CH$_2$)$_{p3}$—X$_3$;
R$_2$ is —H; —CH$_2$-pyrimidine said pyrimidine being optionally substituted in position 2 with —O—(CH$_2$)$_2$—X$_1$;
R$_3$ is —H; or
R$_2$ and R$_3$ form, together with the carbon atoms to which they are attached, a cycloalkane, in particular a cyclopentane or a cyclohexane;
R$_4$ is —H; a lone pair; —(CH$_2$)$_m$—C(=O)—R$_{10}$
  wherein R$_{10}$ is —OH; —O—(C$_1$-C$_3$)alkyl group preferably a methyl or isopropyl group; or —N(—R$_{11}$)(—R$_{12}$)
  wherein
    R$_{11}$ is —H; —(CH$_2$)$_n$—X$_2$; —(CH$_2$)$_n$—C≡CH; —(CH$_2$)$_n$-[(-diethyl)(-methyl)-ammonium]; —(CH$_2$)$_n$—N(R$_{13}$)$_2$ wherein R$_{13}$ is (C$_1$-C$_3$)alkyl preferably an ethyl group;
    R$_{12}$ is selected from —(CH$_2$)$_{n1}$—OH; —(CH$_2$)$_{n1}$—X$_2$; —(CH$_2$)$_n$-Ph-Ph-X$_2$, —(CH$_2$)$_{n1}$-Ph-Ph-(CH$_2$)$_{n2}$—X$_2$; —(CH$_2$)$_{n1}$-Ph-Ph-C≡C—(CH$_2$)$_{n2}$—X$_2$; or (CH$_2$)$_{n1}$-Ph-Ph-O—(CH$_2$)$_{n2}$—X$_2$,
    or R$_{11}$ and R$_{12}$ form, together with the nitrogen atom to which they are attached, a piperazine, said piperazine being optionally substituted in position 4 with -Ph-O—(CH$_2$)$_{n3}$—X$_2$;
R$_5$ is —(CH$_2$)$_o$-Ph-X$_5$; or —(CH$_2$)$_o$-Ph-SnBu$_3$;
R$_6$ is —H, a lone pair; —(CH$_2$)$_r$—C(=O)—R$_9$
  wherein R$_9$ is —OH; —O—(C$_1$-C$_3$)alkyl group, said (C$_1$-C$_3$)alkyl group being preferably an isopropyl group; or —N(—R$_{17}$)(—R$_8$)
  wherein R$_{17}$ is —(CH$_2$)$_{n4}$—N(R$_{19}$)$_2$ wherein R$_{19}$ is (C$_1$-C$_3$)alkyl preferably an ethyl group; R$_{18}$ is —(CH$_2$)$_{n5}$-Ph-Ph-X$_6$;
X$_1$, X$_2$, X$_3$, X$_4$, X$_5$, and X$_6$ each independently represents —$^{18}$F, —$^{124}$I-$^{131}$I, $^{123}$I, $^{125}$I, $^{211}$At, —Cl; —F, —I, —$^{19}$F; —CF$_3$, —OTs, or a group selected from

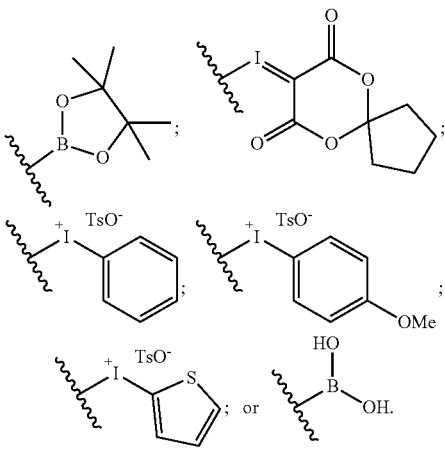

---- denotes a single or double bond;
n, n$_1$, n$_2$, n$_3$, n$_4$, n$_5$, m, o, p, p$_1$, p$_2$, p$_3$, q, and r are integers that are independently equal to 0, 1, 2, 3, 4, 5, 6, 7 or 8, preferably equal to 1, 2, 3 or 4;
with the proviso that at least one of R$_1$', R$_2$, R$_4$ or R$_5$ comprises X$_1$, X$_2$, X$_3$, X$_4$; X$_5$ or X$_6$; and with the proviso that said compound is not Darapladib.

In a particular embodiment, X$_1$, X$_2$, X$_3$, X$_4$, X$_5$ and X$_6$ each independently represents —$^{18}$F, —$^{124}$I-$^{131}$I, $^{123}$I, $^{125}$I, $^{211}$At, —Cl; —I, —CF$_3$, —OTs, or a group selected from

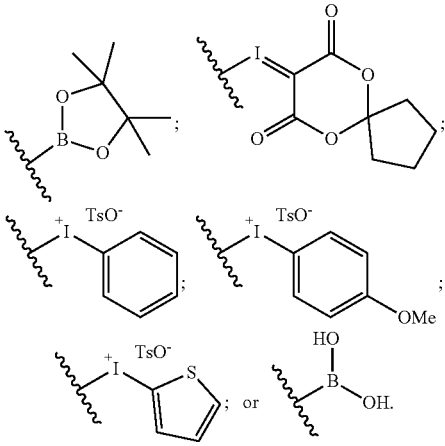

As used herein, the term "Darapladib" refers to the drug of general formula (I) as previously defined, wherein:
R$_1$ is =O,
R$_2$ and R$_3$ form, together with the carbon atoms to which they are attached, a cyclopentane,
R$_4$—(CH$_2$)—C(=O)—R$_{10}$,
  wherein R$_{10}$ represents —N(—R$_{11}$)(—R$_{12}$),
  wherein R$_{11}$ represents —(CH$_2$)$_2$—N(R$_{13}$)$_2$ wherein R$_{13}$ is an ethyl group,
  wherein R$_{12}$ represents (CH$_2$)-Ph-Ph-CF$_3$,
R$_5$ represents —(CH$_2$)-Ph-F,
R$_6$ represents a lone pair.

The expression "C$_1$-C$_3$ alkyl group" represents a linear or branched alkyl group having from 1 to 3 carbons atoms. Examples of such alkyl groups include methyl, ethyl, n-propyl or i-propyl.

In a particular embodiment, in the formula (I) as previously defined R$_9$ is not —N(—R$_{17}$)(—R$_{18}$) wherein R$_{17}$ is —(CH$_2$)$_{n4}$—N(R$_{19}$)$_2$ wherein R$_{19}$ is (C$_1$-C$_3$)alkyl preferably an ethyl group; and wherein R$_{18}$ is —(CH$_2$)$_{n5}$-Ph-Ph-X$_6$.

In a particular embodiment, in the formula (I) as previously defined at least one of R$_{1'}$, R$_2$, R$_4$, R$_5$ or R$_6$ comprises —$^{18}$F, —$^{124}$I-$^{131}$I, $^{123}$I, $^{125}$I, $^{211}$At, —OTs, SnBu$_3$ or a group selected from:

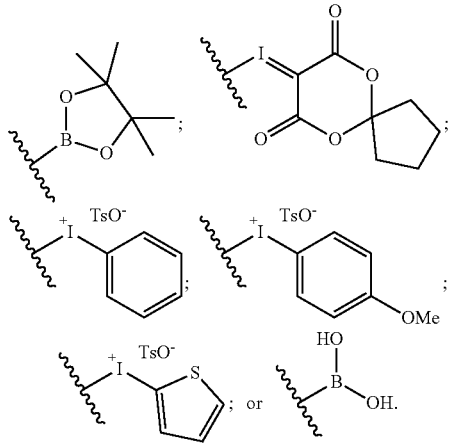

In a particular embodiment, in the formula (I) as previously defined R$_2$ and R$_3$ form, together with the carbon atoms to which they are attached, a cyclopentane or a cyclohexane; and R$_5$ is —(CH$_2$)-Ph-X$_5$; or —(CH$_2$)-Ph-SnBu$_3$.

In a particular embodiment, in the formula (I) as previously defined R$_1$ is =O or —O—R$_{1'}$ wherein R$_{1'}$ is —(CH$_2$)—C(=O)—R$_7$ or —(CH$_2$)—C(=O)—O—R$_8$
wherein R$_8$ represents the following group:

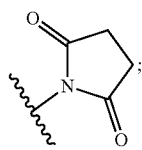 [SMILES: *N1C(=O)CCC1=O]

and
wherein R$_7$ is —OH; —O-isopropyl group; —N(—R$_{14}$)(—R$_{15}$);
wherein
R$_{14}$ is —H; —(CH$_2$)$_2$—N(R$_{16}$)$_2$ wherein R$_{16}$ is an ethyl group;
R$_{15}$ is selected from —(CH$_2$)$_4$—X$_4$; —(CH$_2$)-Ph-Ph-X$_4$.

In a particular embodiment, in the formula (I) as previously defined R$_4$ is —H; a lone pair; —(CH$_2$)—C(=O)—R$_{10}$
wherein R$_{10}$ is —OH; —O-isopropyl group; or —N(—R$_{11}$)(—R$_{12}$)
wherein
R$_{11}$ is —H; —(CH$_2$)$_2$—X$_2$; —(CH$_2$)$_2$-[(-diethyl)(-methyl)-ammonium]; —(CH$_2$)$_2$—N(R$_{13}$)$_2$ wherein R$_{13}$ is an ethyl group;
R$_{12}$ is selected from —(CH$_2$)$_2$—X$_2$; —(CH$_2$)$_4$—X$_2$; —(CH$_2$)-Ph-Ph-X$_2$, —(CH$_2$)$_1$-Ph-Ph-(CH$_2$)$_2$—X$_2$; —(CH$_2$)-Ph-Ph-C≡C—(CH$_2$)$_2$—X$_2$; or —(CH$_2$)$_1$-Ph-Ph-O—(CH$_2$)$_2$—X$_2$,
or R$_{11}$ and R$_{12}$ form, together with the nitrogen atom to which they are attached, a piperazine, said piperazine being optionally substituted in position 4 with -Ph-O—(CH$_2$)$_2$—X$_2$.

In a particular embodiment, in the formula (I) as previously defined R$_6$ is —H, a lone pair; —(CH$_2$)—C(=O)—R$_9$
wherein R$_9$ is —OH; —O-isopropyl group; or —N(—R$_{17}$)(—R$_8$)
wherein R$_{17}$ is —(CH$_2$)$_2$—N(R$_{19}$)$_2$ wherein R$_{19}$ is an ethyl group;
R$_{18}$ is —(CH$_2$)-Ph-Ph-X$_6$.

In a particular embodiment, the compound of formula (I) is selected from the group consisting of A1 to A56.

Those compounds are described in Table 1 hereinafter.

TABLE 1

| | Formula | IC50 |
|---|---|---|
| A1 | ![A1 structure] | |
| A2 | ![A2 structure] | |

X = $^{18}$F, $^{124}$I, $^{131}$I, $^{123}$I, $^{125}$I or $^{211}$At

TABLE 1-continued

| | Formula | IC50 |
|---|---|---|
| A3 | | |
| A4 | | IC$_{50}$ (X = $^{19}$F) = 50 nM |
| | X = $^{19}$F | |
| | X = $^{18}$F, $^{124}$I, $^{131}$I, $^{123}$I, $^{125}$I or $^{211}$At | |
| A5 | | |
| A6 | | |
| | X = $^{18}$F, $^{124}$I, $^{131}$I, $^{123}$I, $^{125}$I or $^{211}$At | |

TABLE 1-continued

| | Formula | IC50 |
|---|---|---|
| A7 | | |
| A8 | | |
| | X = $^{18}$F, $^{124}$I, $^{131}$I, $^{123}$I, $^{125}$I or $^{211}$At | |
| A9 | | |
| A10 | | |
| | X = $^{18}$F, $^{124}$I, $^{131}$I, $^{123}$I, $^{125}$I or $^{211}$At | |
| A11 | | |

TABLE 1-continued
| | Formula | IC50 |
|---|---|---|
| A12 | 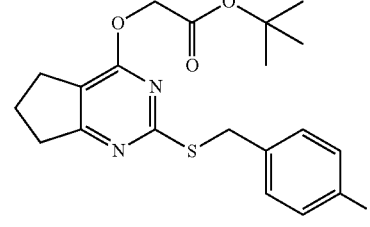
X = $^{18}$F, $^{124}$I, $^{131}$I, $^{123}$I, $^{125}$I or $^{211}$At | |
| A13 | 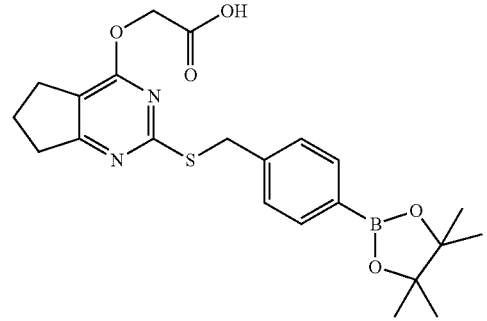 [SMILES: CC1(C)OB(c2ccc(CSc3nc4c(c(OCC(=O)O)n3)CCC4)cc2)OC1(C)C] | |
| A14 | 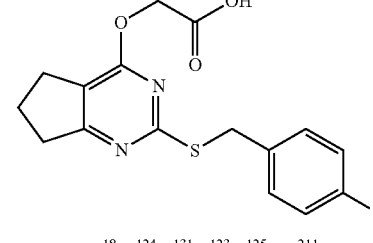
X = $^{18}$F, $^{124}$I, $^{131}$I, $^{123}$I, $^{125}$I or $^{211}$At | |
| A15 | 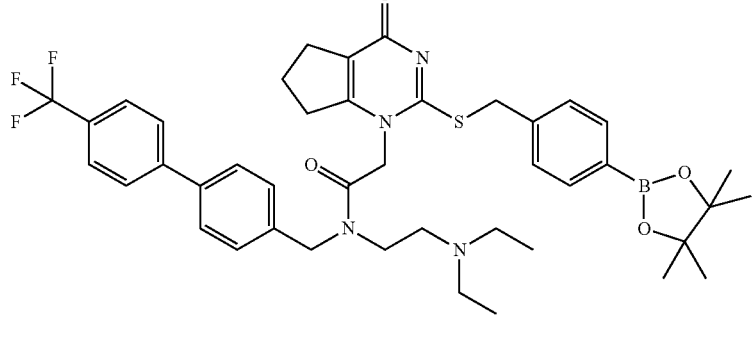 | |
| A16 | 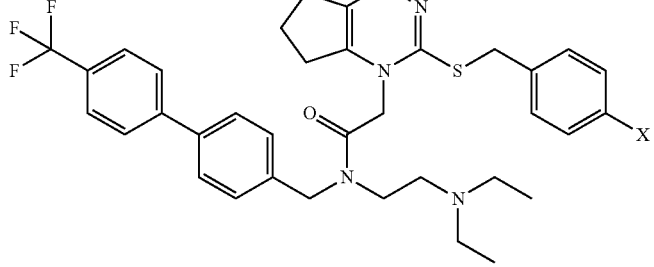
X = $^{18}$F, $^{124}$I, $^{131}$I, $^{123}$I, $^{125}$I or $^{211}$At | |

TABLE 1-continued

| Formula | IC50 |
|---|---|

A17

A18

X = ¹⁸F, ¹²⁴I, ¹³¹I, ¹²³I, ¹²⁵I or ²¹¹At

A19

A20

TABLE 1-continued
| Formula | IC50 |
|---|---|
A21
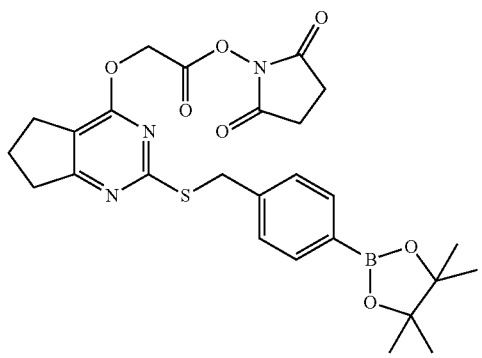 [SMILES: CC1(C)OB(c2ccc(CSc3nc4c(c(OCC(=O)ON5C(=O)CCC5=O)n3)CCC4)cc2)OC1(C)C]
A22
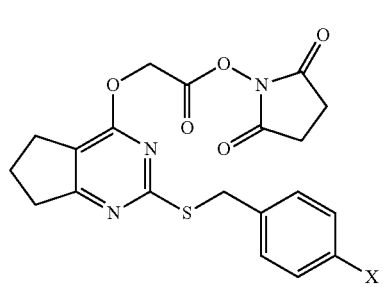
X = $^{18}$F, $^{124}$I, $^{131}$I, $^{123}$I, $^{125}$I or $^{211}$At
A23
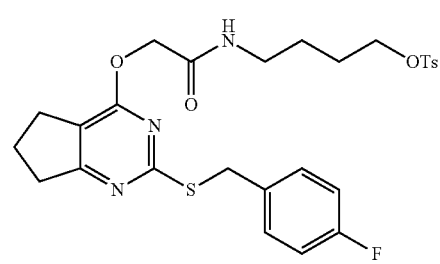 [SMILES: Cc1ccc(S(=O)(=O)OCCCCNC(=O)COc2nc(SCc3ccc(F)cc3)nc3c2CCC3)cc1]
A24
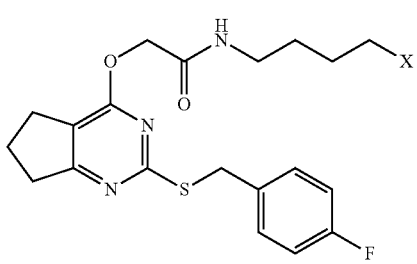
X = $^{18}$F, $^{124}$I, $^{131}$I, $^{123}$I, $^{125}$I or $^{211}$At
A25
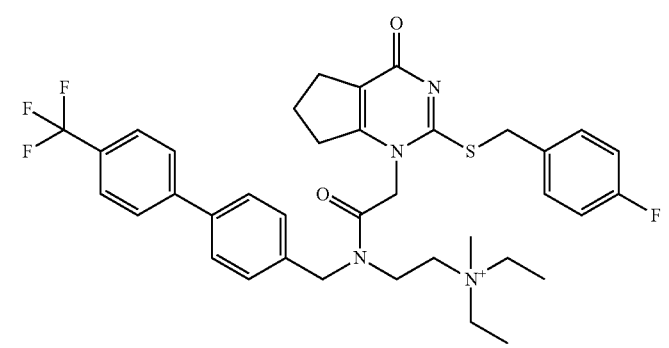 [SMILES: CC[N+](C)(CC)CCN(Cc1ccc(-c2ccc(C(F)(F)F)cc2)cc1)C(=O)Cn1c(SCc2ccc(F)cc2)nc(=O)c2c1CCC2]

TABLE 1-continued

| Formula | IC50 |
|---|---|

A26

X = $^{18}$F, $^{124}$I, $^{131}$I, $^{123}$I, $^{125}$I or $^{211}$At

A27

A28

A29

X = $^{18}$F, $^{124}$I, $^{131}$I, $^{123}$I, $^{125}$I or $^{211}$At

A30

TABLE 1-continued
| | Formula | IC50 |
|---|---|---|
| A31 | 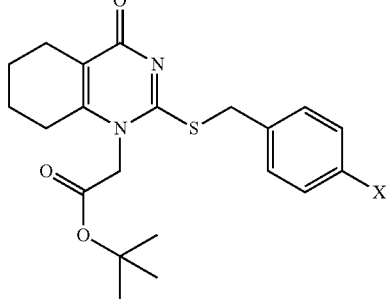 X = $^{18}$F, $^{124}$I, $^{131}$I, $^{123}$I, $^{125}$I or $^{211}$At | |
| A32 | 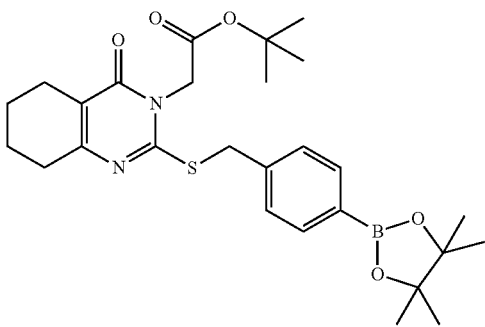 [SMILES: CC(C)(C)OC(=O)Cn1c(SCc2ccc(B3OC(C)(C)C(C)(C)O3)cc2)nc2c(c1=O)CCCC2] | |
| A33 | 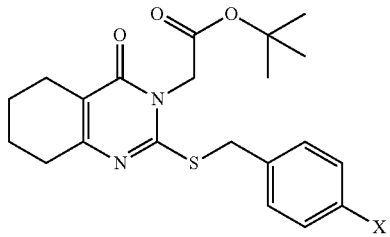 X = $^{18}$F, $^{124}$I, $^{131}$I, $^{123}$I, $^{125}$I or $^{211}$At | |
| A34 | 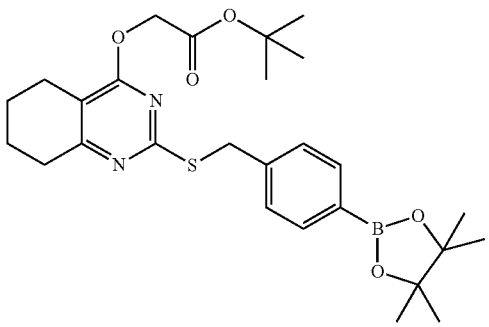 [SMILES: CC(C)(C)OC(=O)COc1nc(SCc2ccc(B3OC(C)(C)C(C)(C)O3)cc2)nc2c1CCCC2] | |
| A35 | 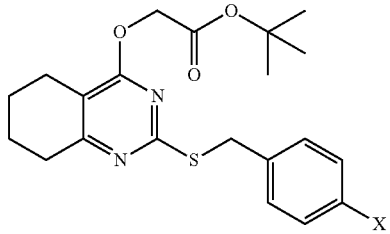 X = $^{18}$F, $^{124}$I, $^{131}$I, $^{123}$I, $^{125}$I or $^{211}$At | |

TABLE 1-continued

| | Formula | IC50 |
|---|---|---|
| A36 | 4-oxo-5,6,7,8-tetrahydroquinazoline N1-substituted with CH2C(=O)NH-(CH2)4-OTs; 2-S-CH2-(4-fluorophenyl) | |
| A37 | 4-oxo-5,6,7,8-tetrahydroquinazoline N1-substituted with CH2C(=O)NH-(CH2)4-X; 2-S-CH2-(4-fluorophenyl); X = $^{18}$F, $^{124}$I, $^{131}$I, $^{123}$I, $^{125}$I or $^{211}$At | |
| A38 | 4-oxo-5,6,7,8-tetrahydroquinazoline N1-substituted with CH2COOH; 2-S-CH2-(4-(4,4,5,5-tetramethyl-1,3,2-dioxaborolan-2-yl)phenyl) | |
| A39 | 4-oxo-5,6,7,8-tetrahydroquinazoline N1-substituted with CH2COOH; 2-S-CH2-(4-X-phenyl); X = $^{18}$F, $^{124}$I, $^{131}$I, $^{123}$I, $^{125}$I or $^{211}$At | |
| A40 | 4-oxo-6,7-dihydro-5H-cyclopenta[d]pyrimidine N1-substituted with CH2C(=O)NH-(CH2)4-OTs; 2-S-CH2-(4-fluorophenyl) | |

TABLE 1-continued
| Formula | IC50 |
|---|---|
A41
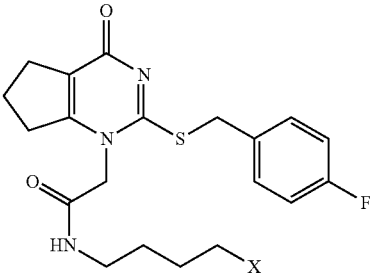 [SMILES: Cc1ccc(S(=O)(=O)OCCCCNC(=O)Cn2c(SCc3ccc(F)cc3)nc(=O)c3c2CCC3)cc1]
X = ¹⁸F, ¹²⁴I, ¹³¹I, ¹²³I, ¹²⁵I or ²¹¹At
A42
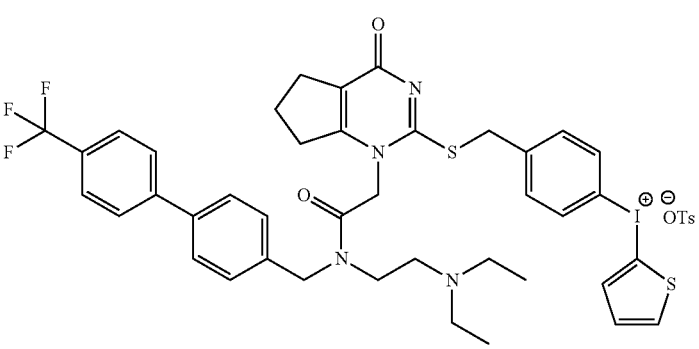 [SMILES: CCN(CC)CCN(Cc1ccc(-c2ccc(C(F)(F)F)cc2)cc1)C(=O)Cn1c(SCc2ccc([I+]c3cccs3)cc2)nc(=O)c2c1CCC2]
A43
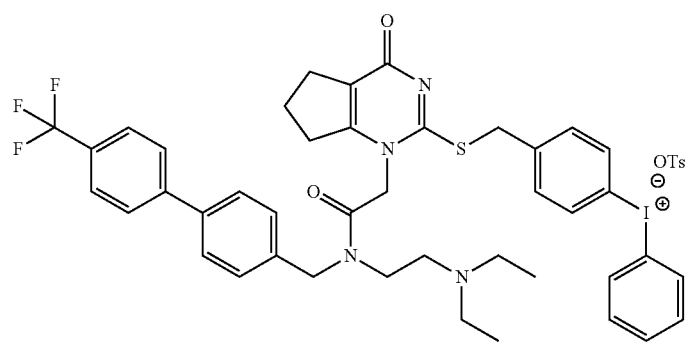 [SMILES: CCN(CC)CCN(Cc1ccc(-c2ccc(C(F)(F)F)cc2)cc1)C(=O)Cn1c(SCc2ccc([I+]c3ccccc3)cc2)nc(=O)c2c1CCC2]
A44
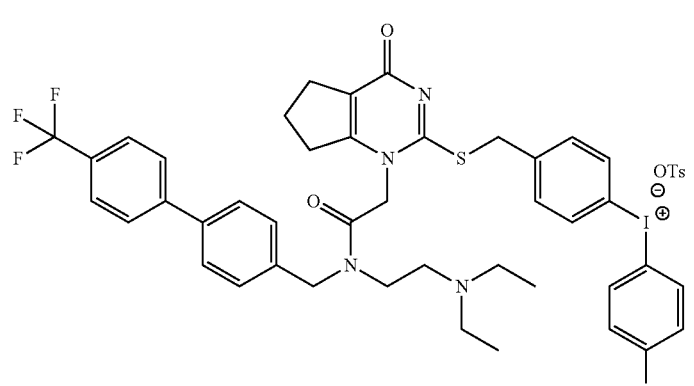

TABLE 1-continued

| Formula | IC50 |
|---|---|
| A45 | |
| A46 | |
| A47 X = $^{18}$F, $^{124}$I, $^{131}$I, $^{123}$I, $^{125}$I or $^{211}$At | |
| A48 | |

TABLE 1-continued

| Formula | IC50 |
|---|---|

A49

X = $^{18}$F, $^{124}$I, $^{131}$I, $^{123}$I, $^{125}$I or $^{211}$At

A50

A51

A52

X = $^{18}$F, $^{124}$I, $^{131}$I, $^{123}$I, $^{125}$I or $^{211}$At

TABLE 1-continued

| | Formula | IC50 |
|---|---|---|
| A53 | | |
| A54 | | |
| | X = $^{18}$F, $^{124}$I, $^{131}$I, $^{123}$I, $^{125}$I or $^{211}$At | |
| A55 | | |
| A56 | | |
| | X = $^{18}$F, $^{124}$I, $^{131}$I, $^{123}$I, $^{125}$I or $^{211}$At | |

| Formula | IC50 |
|---|---|
| A57 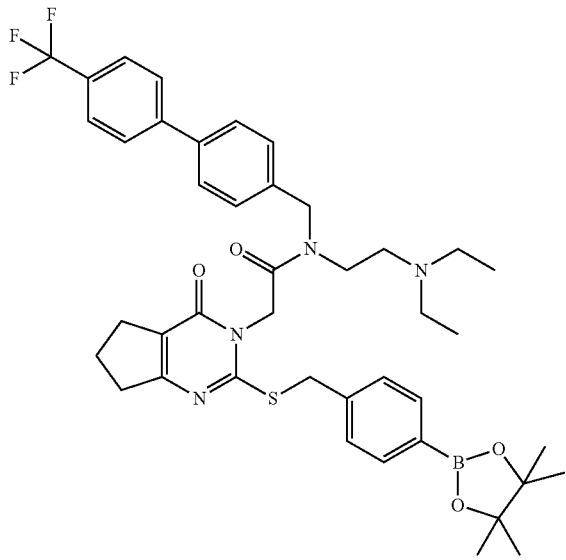 | |
| A58 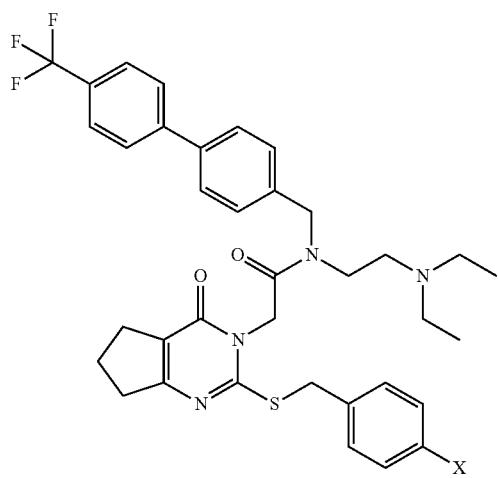 X = $^{18}$F, $^{124}$I, $^{131}$I, $^{123}$I, $^{125}$I or $^{211}$At | |
Another object of the present invention refers to a process for preparing the compound of formula (I) as previously defined comprising the steps of:
reacting a compound of general formula (II) or (III):
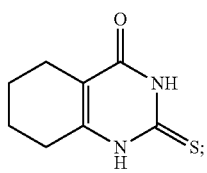
(II)
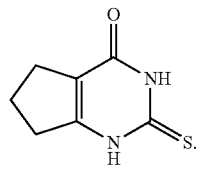
(III)
In a particular embodiment, the compounds of general formula (II) or (III) may react with a compound of formula (IV):

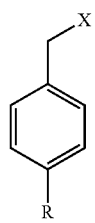

wherein R represents a group selected from:

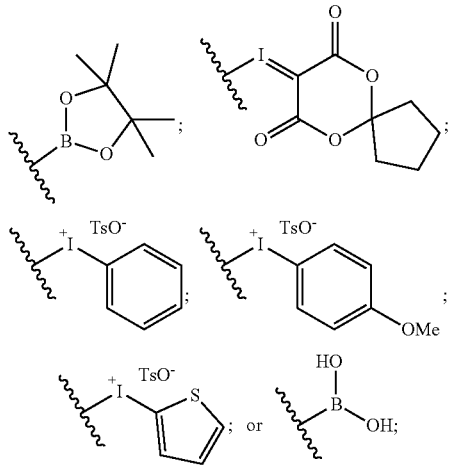

or R represents —$^{19}$F, —$^{18}$F, —$^{124}$I-$^{131}$I, $^{123}$I, $^{125}$I or $^{211}$At;

and X represents an halogen or a leaving group such as CF$_3$, I, Br, Cl, OTs, OTf or Oms.

The compound of formula (IV) is described in scheme 8 below.

In a particular embodiment, the compound of general formula (II) is obtained by reacting a compound of formula (IIA) with a compound of formula (IIB) in the presence of 1,8-Diazabicyclo(5.4.0)undec-7-ene (DBU) and Acetonitrile (ACN):

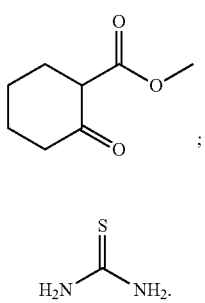

In a particular embodiment, the compound of general formula (III) is obtained by reacting a compound of formula (IIIA) with a compound of formula (IIIB) in the presence of 1,8-Diazabicyclo(5.4.0)undec-7-ene (DBU) and Acetonitrile (ACN):

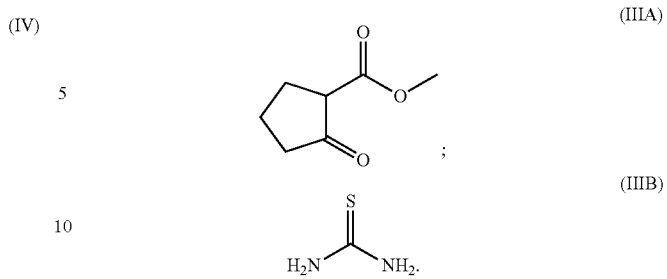

Another object of the present invention is a compound of formula (I) as previously defined, wherein at least one of X$_1$, X$_2$, X$_3$, X$_4$, X$_5$ or X$_6$ is $^{18}$F, $^{124}$I, $^{131}$I, $^{123}$I, $^{125}$I or $^{211}$At.

In a particular embodiment, said compound is an imaging agent able to target Lp-PLA$_2$.

As used herein, the term "imaging agent" refers to a compound that can be used to detect specific biological elements (e.g., biomolecules) using imaging techniques. Imaging agents of the present invention can be used to detect Lp-PLA$_2$ in in vitro and ex vivo biological systems as well as in subjects.

As used herein, the term "Lp-PLA$_2$" refers to the lipoprotein-associated phospholipase A$_2$, which is an enzyme produced by inflammatory cells involved in atherogenesis (Chem. Rev. 2011, 111, 6130-6185). Studies have shown that Lp-PLA$_2$ was also involved in Neonatal Necrotizing Enterocolitis (Caplan, M.; Hsueh, W.; Kelly, A.; Donovan, M. Prostaglandins 1990, 39, 705), cancers (pancreatic cancer), rheumatoid arthritis etc.

In another embodiment, imaging agents of the present invention are used to detect the accumulation of inflammatory cells and/or lipoproteins (LDL and/or HDL).

Another object of the present invention is a process for preparing the compound of formula (I) as previously defined comprising the steps of:

providing a compound of formula (I) wherein at least one of X$_1$, X$_2$, X$_3$, X$_4$ X$_5$ or X$_6$ is —Cl; —F, —I, —$^{19}$F; —CF$_3$, —OTs, or a group selected from:

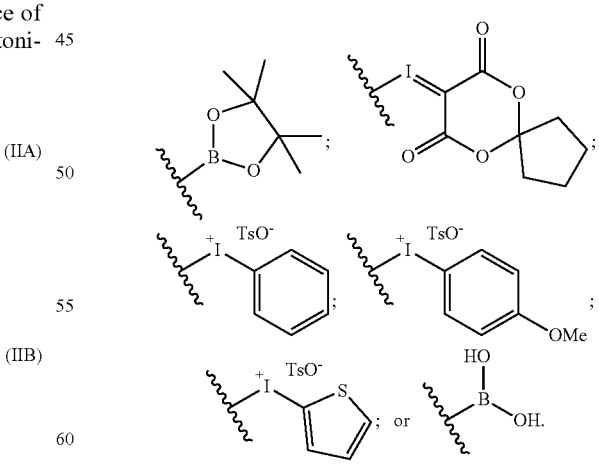

reacting said compound with a salt of $^{18}$F, $^{124}$I, $^{131}$I, $^{123}$I, $^{125}$I or $^{211}$At, in the presence of [Cu(OTf)$_2$(Py)$_4$] or [Cu(OTf)$_2$].

As used herein, the term "salt of $^{18}$F, $^{124}$I, $^{131}$I, $^{123}$I $^{125}$I or $^{211}$At" refers to ionic compounds consisting of at least one cation selected from $K^+$, $Et_4N^+$, $Na^+$, $Cs^+$ and $Bu_4N^+$ and at least one anion selected from $^8F^-$, $^{124}I^-$ and $^{131}I^-$.

Another object of the present invention is a method for detecting Lp-PLA$_2$ enzyme in a patient, said method comprising the steps of:
    administering to said patient a detectable amount of the compound of formula (I) as previously defined,
    subjecting said patient to PET or SPECT,
    collecting the PET or SPECT signal.

As used herein, the term "patient" refers to a human or another mammal (e.g., mouse, rat, rabbit, hamster, dog, cat, cattle, swine, sheep, horse or primate).

As used herein, the term "PET" refers to Positron Emission Tomography which is an imaging technique.

As used herein, the term "SPECT" refers to Single-photon emission computed tomography which is an imaging technique.

Another object of the present invention is a method for detecting atherosclerotic plaques, in particular vulnerable atherosclerotic plaques, in a patient, said method comprising the steps of:
    administering to said patient a detectable amount of the compound of formula (I) as previously defined,
    subjecting said patient to PET or SPECT,
    collecting the PET or SPECT signal.

As used herein, the term "vulnerable atherosclerotic plaques" refers to plaques characterized by a high number of inflammatory cells (leukocytes and phagocytic cells) and proteic biomarkers and/or to plaques that are susceptible to break.

In a particular embodiment, the compound of formula (I) as previously defined is administered to said patient by intra-venous, subcutaneous or oral route.

In a particular embodiment, blood vessels of the patient are subjected to PET or SPECT, in particular blood vessels of the heart, brain, liver, pancreas, spleen, kidney, bladder and intestine and lung, and more particularly the carotid, coronary, femoral and cerebral arteries.

As used herein, the term "blood vessels" refers to arteries and veins.

In a particular embodiment, the bones, muscles, brain, aorta, stomach and thyroid of the patient are subjected to PET or SPECT.

BRIEF DESCRIPTION OF DRAWINGS

FIG. 5:
Injection of [18F]Darapladib in C57Bl6 (17 MBq) (ex vivo—after dissection of the heart and aorta of the mice).
Accumulation in the heart (presence of blood through the coronary arteries).
No accumulation along the aorta (no atheroma plaques).
From left to right, transverse, coronal and sagittal views.

FIGS. 6A and 6B:
Injection of [18F]-FDG in ApoE KO (FIG. 6A) and C57Bl6 (FIG. 6B) (Whole body PET imaging).
Accumulation in the brain, heart, kidneys and bladder.
From left to right, transverse, coronal and sagittal views.

FIGS. 7A and 7B:
Injection of [18F]-FDG in ApoE KO (FIG. 7A) and C57Bl6 (FIG. 7B) (heart and aorta).
Accumulation in the heart (presence of blood through the coronary arteries and glucose uptake through the myocardium).
No accumulation along the aorta (with atheroma plaques: ApoE—and without atheroma plaques: C57Bl6). From left to right, transverse, coronal and sagittal views.

FIG. 8:
Distribution table—biodistribution studies

FIG. 12A:
Ex-vivo—macroscopic view of ApoE KO mice aorta after injection of [18F]-FDG.
Plaques but no labelling.

FIG. 12B:
Ex-vivo—macroscopic view of ApoE KO mice aorta after injection of [18F]-Darapladib.
Plaques and labelling along the aorta.

FIG. 13A:
Ex-vivo—macroscopic view of C57Bl6 (WT) mice aorta after injection of [18F]-FDG.
No plaques and no labelling.

FIG. 13B:
Ex-vivo—macroscopic view of C57Bl6 (WT) mice aorta after injection of [18F]-Darapladib.
No plaques and no labelling.

FIG. 14A:
In vivo—Injection of [18F]N1-FGU (herein referred as compound A4) in C57BL/6 mice (PET imaging).

FIG. 14B:
In vivo—Injection of [18F]N1-FGU (herein referred as compound A4) in ApoE KO mice (PET imaging).

FIG. 15A:
Ex-vivo—macroscopic view of C57BL/6 mice heart/aorta after injection of [18F]N1-FGU (herein referred as compound A4)

FIG. 15B:
Ex-vivo—macroscopic view of ApoE KO mice heart/aorta after injection of [18F]N1-FGU (herein referred as compound A4)

FIG. 16A:
Ex-vivo—macroscopic view of human carotid endarterectomy samples with [18F]FDG FIG. 16B:
Ex-vivo—macroscopic view of human carotid endarterectomy samples with [18F]N1-FGU (herein referred as compound A4)

FIG. 17A:
In vivo—Injection of $^{18}$F—O-FGU (herein referred as compound A12) in ApoE KO mice (Whole body PET imaging).

FIG. 17B:
In vivo—Injection of $^{18}$F—O-FGU (herein referred as compound A12) in C57BL/6 mice (Whole body PET imaging).

EXAMPLES

Example 1

Figure 1:
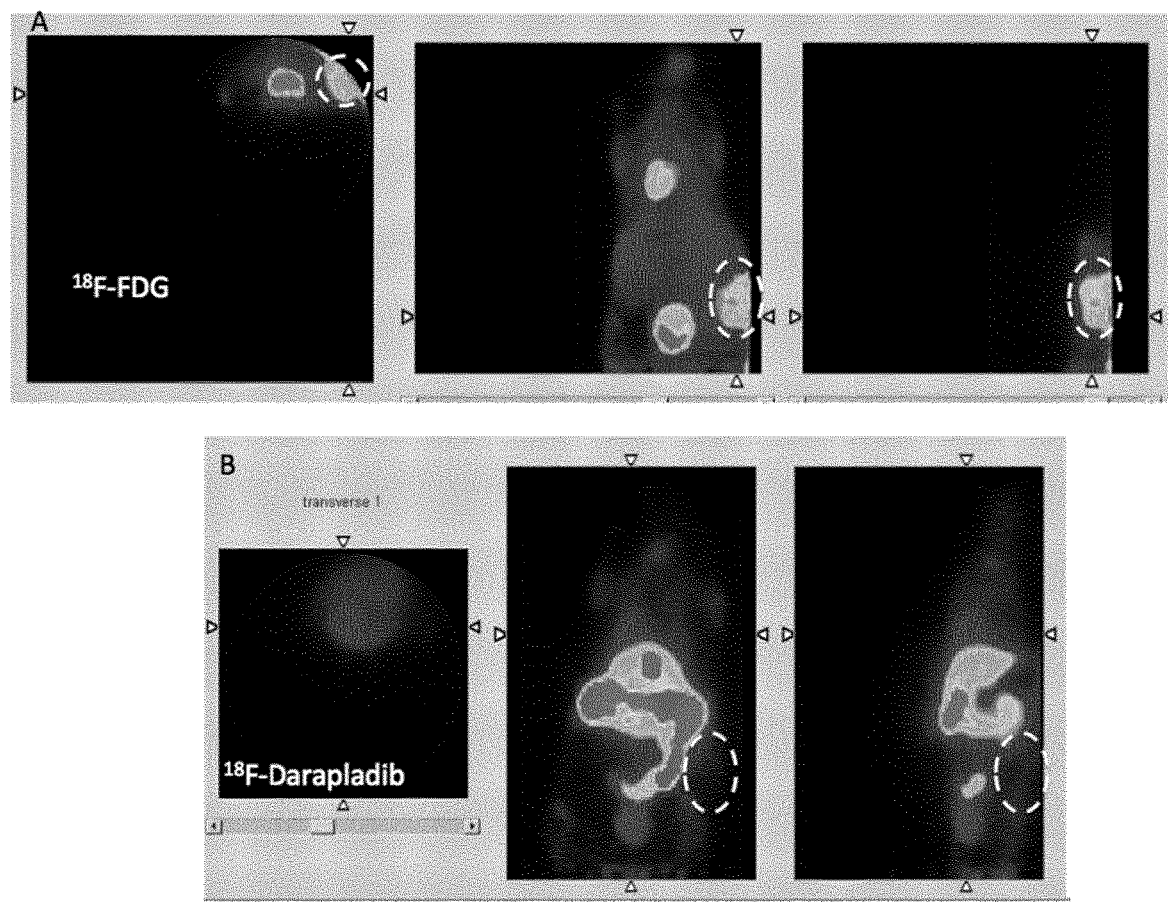
FIG. 1:
Injection of [18F]-FDG (A) and [18F]Darapladib (B) in tumor-induced C57/Bl6 mice (19 MBq and 9 MBq—respectively, Whole body PET imaging). [18F]-FDG accumulation in the tumor (dashed circle). Absence of [18F]Darapladib in the tumor (dashed circle). From left to right, transverse, coronal and sagittal views.

1. Chemical Synthesis 1.1. General Materials and Methods

Unless otherwise noted, all reagents were purchased from commercial suppliers and used without further purification (Acros and Sigma-Aldrich). Pyridine and DiPEA were distilled prior to use. All the solvents were purchased from Carlo-Erba. Solvents used for synthesis were dried under standard conditions. Reactions were carried out under argon atmosphere in air-dried glassware when needed. Sensitive liquids were transferred via syringe. Thin layer chromatographies were performed using TLC silica gel coated aluminum plates (Macherey-Nagel, SilG$_{60}$/UV$_{254}$).

$^1$H, $^{13}$C NMR spectra were recorded on a Bruker Advanced 3 spectrometer at 25° C. (600 MHz for $^1$H and 150 MHz for $^{13}$C). Chemical shifts are reported in parts per million (ppm) relative to trimethylsilane (TMS) and calibrated using solvent residual peaks (CDCl$_3$ or DMSO-d$_6$). $^1$H NMR multiplicities are reported as follows: s=singlet, d=doublet, t=triplet, q=quartet, quint=quintet, m=multiplet, bs=broad signal.

All HPLC Analysis were performed on a Thermofisher UPLC Ultimate 3000 system equipped with a UV-Vis spectrophotometer with diode array detector; column: Gemini C18 250×4.6 mm, 5 µm (Phenomenex), isocratic elution: NH$_4$OAc 0.1M (pH 6)/MeCN 50/50; flow rate: 1 ml/min; room temperature.

1.2. Synthesis of Alkylating Agent

Scheme 1. Synthesis of alkylating agent 3

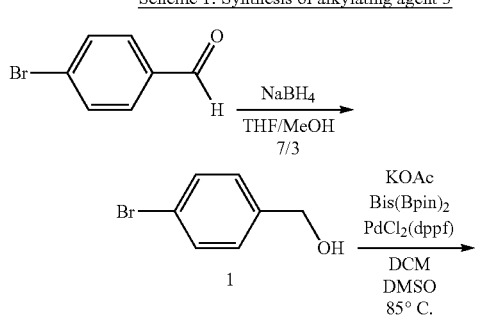

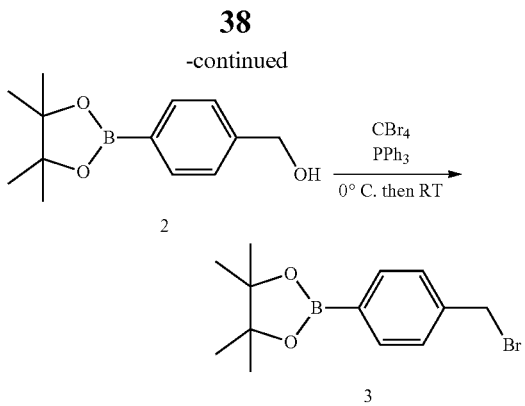

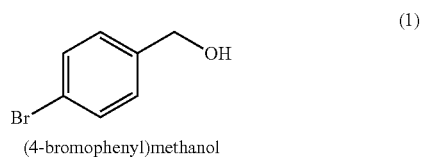

(1)

(4-bromophenyl)methanol

Bromobenzaldehyde (1 eq, 5.40 mmol) was dissolved in THF/MeOH (7/3 v/v; 32/13 mL). The reaction was cooled to 0° C. with an ice bath then sodium borohydride (1.5 eq, 8.10 mmol) was added with caution portion wise. The mixture was then stirred at rt for 30 min. HCl 1N was added to quench unreacted hydride. The reaction was extracted using DCM 3 times (3×10 mL) then the combined organic extracts were washed with water and brine followed by drying and filtering. Removal of the solvent under reduced pressure afforded the desired compound as a colourless solid (953 mg, 91%).

$^1$H-NMR (CDCl$_3$, 600 MHz) δ 7.48 (d, J=8.2 Hz, 2H), 7.23 (d, J=8.2 Hz, 2H), 4.65 (s, 2H); $^{13}$C-NMR (CDCl$_3$, 150 MHz) δ 140.0, 131.8, 128.7, 121.6, 64.7.

(4-(4,4,5,5-Tetramethyl-1,3,2-dioxaborolan-2-yl)phenyl)methanol (2)

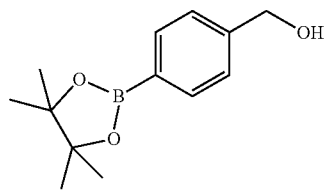 [SMILES: CC1(C)OB(c2ccc(CO)cc2)OC1(C)C]

The compound 1 (1 eq, 0.53 mmol) was dissolved in DMSO (2 mL) followed by the addition of potassium acetate (3 eq, 1.59 mmol), bis(pinacolato)diboron (1.1 eq, 0.59 mmol) and Pd(dppf)Cl$_2$ (0.2 eq, 0.11 mmol). The mixture was deoxygenated by three successive argon bubbling/vacuum cycles. The reaction was then heated at 85° C. under argon for 18 h. Water (5 mL) was added and the resulting black solution was extracted 3 times with EtOAc (3×10 mL). The combined organic extracts were washed with brine, dried, filtered and evaporated under vacuum. The resulting paste was purified using column chromatography (silica gel, 70/30 Hex/EtOAc) to afford the desired compound (Rf=0.3) as a colourless oil (113 mg, 91%).

$^1$H-NMR (CDCl$_3$, 600 MHz) δ 7.79 (d, J=7.7 Hz, 2H), 7.36 (d, J=7.7 Hz, 2H), 4.71 (s, 2H), 1.35 (s, 12H); $^{13}$C-NMR (CDCl$_3$, 150 MHz) δ 144.1, 135.2, 126.2, 83.9, 65.4, 25.0.

2-(4-(Bromomethyl)phenyl)-4,4,5,5-tetramethyl-1,3,2-dioxaborolane (3)

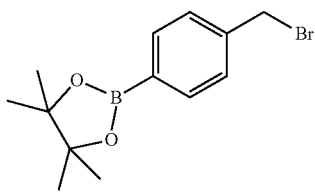 [SMILES: CC1(C)OB(c2ccc(CBr)cc2)OC1(C)C]

The compound 2 (1 eq, 5.72 mmol) was dissolved in THF (25 mL) followed by the addition of triphenylphosphine (2 eq, 11.4 mmol). The mixture was cooled to 0° C. with an ice bath then tetrabromomethane (2 eq, 11.4 mmol) was carefully added portion wise. The reaction was stirred at rt for 18 h. The solution was poured into water (30 mL) and extracted 3 times (3×25 mL) with EtOAc. The combined organic extracts were dried, filtered and evaporated under vacuum. The compound was purified using column chromatography (silica gel, 99/1 Hex/EtOAc) to afford the desired compound (Rf=0.2) as a colourless solid (1.6 g, 94%).

$^1$H-NMR (CDCl$_3$, 600 MHz) δ 7.78 (d, J=8.0 Hz, 2H), 7.38 (d, J=8.0 Hz, 2H), 4.49 (s, 2H), 1.34 (s, 12H); $^{13}$C-NMR (CDCl$_3$, 150 MHz) δ 140.8, 135.3, 128.4, 84.0, 33.4, 25.0.

1.3. Synthesis of Radiolabelling Precursors 6 and 9

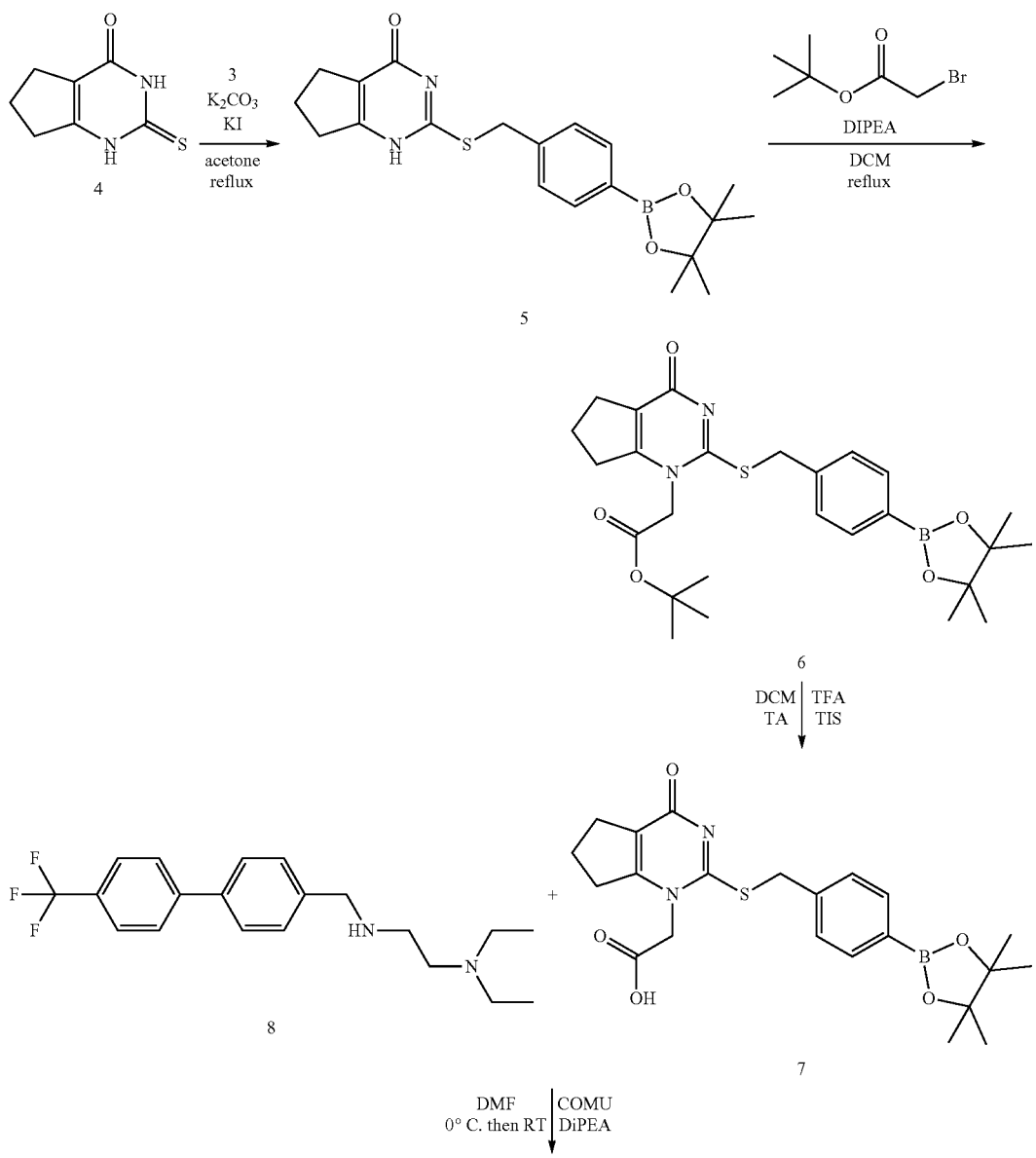

-continued

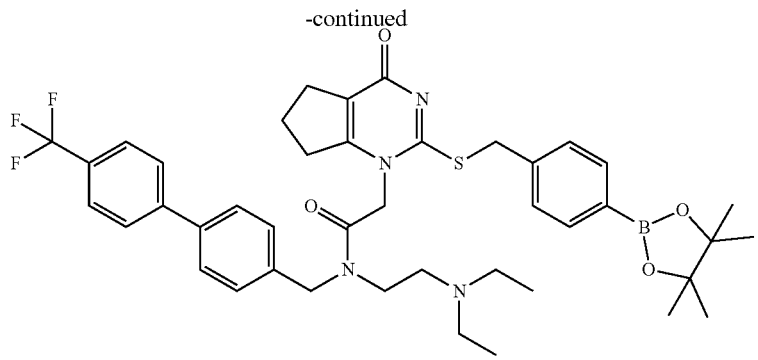

9

2-thioxo-1,2,3,5,6,7-hexahydro-4H-cyclopenta[d]pyrimidin-4-one (4)

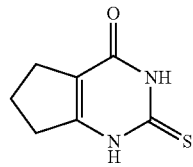 [SMILES: O=c1[nH]c(=S)[nH]c2c1CCC2]

Thiourea (1.5 eq, 21.10 mmol) was stirred in ACN (40 mL). Methyl 2-cyclopentanone-carboxylate (1 eq, 14.07 mmol) was then added followed by DBU (1.2 eq, 16.88 mmol). The mixture was stirred at reflux (ca 82° C.) for 16 h. The reaction was cooled to 0° C. with an ice bath and water (30 mL) was added. The pH was adjusted to 1 using concentrated HCL and the suspension was stirred for 30 min (pH was readjusted to 1 if needed and stirred again for another 30 min). The solid thus obtained was filtered and washed thoroughly with water many times and dried at 55° C. overnight to afford the desired compound as a beige solid (1.540 g, 65%).

$^1$H-NMR (DMSO-$d_6$, 600 MHz) δ 2.67 (t, J=7.5 Hz, 2H), 2.46 (t, J=7.5 Hz, 2H), 1.94 (quint, J=7.5 Hz, 2H); $^{13}$C-NMR (DMSO-$d_6$, 150 MHz) δ 176.2, 160.2, 157.2, 116.1, 31.6, 27.2, 21.4; ESI-MS m/z for $C_7H_8N_2OS$ [MH]$^+$ 169.5, [MNa]$^+$ 191.4;

2-(4-(4,4,5,5-tetramethyl-1,3,2-dioxaborolan-2-yl)benzylthio)-6,7-dihydro-1H-cyclopenta[d]pyrimidin-4(5H)-one (5)

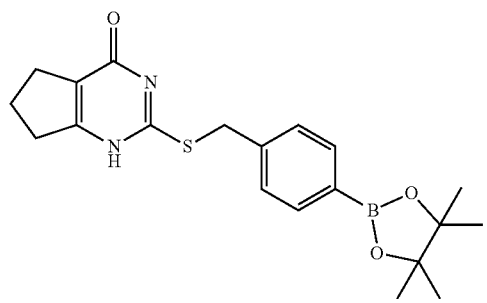 [SMILES: CC1(C)OB(c2ccc(CSc3nc(=O)c4c([nH]3)CCC4)cc2)OC1(C)C]

Compound 4 (1 eq, 0.48 mmol), potassium carbonate (1.5 eq, 0.72 mmol) and potassium iodide (0.1 eq, 0.048 mmol) were stirred in acetone (3 mL) at rt. Compound 3 (1.05 eq, 0.50 mmol) was then added and the mixture was refluxed (54° C.) for 1 h. An additional portion of potassium carbonate (0.2 eq, 0.14 mmol) was poured into the flask and the reflux was maintained for 2 h. After cooling with an ice bath to 0° C., the pH was adjusted to 1 using concentrated HCl. The reaction was stirred for 30 min 1. The solid was then filtered and washed 3 times with water (5 mL×3) then dried at 55° C. to afford the desired compound as a colourless solid (170 mg, 98%).

$^1$H-NMR (DMSO-$d_6$, 600 MHz) δ 7.58 (d, J=8.0 Hz, 2H), 7.39 (d, J=8.0 Hz, 2H), 4.37 (s, 2H), 2.73 (t, J=6.7 Hz, 2H), 2.56 (t, J=6.7 Hz, 2H), 1.93 (quint, J=6.7 Hz, 2H), 1.26 (s, 12H); $^{13}$C-NMR (DMSO-$d_6$, 150 MHz) δ 168.1, 159.1, 140.7, 134.5, 128.6, 83.6, 40.0, 34.3, 33.5, 29.0, 26.7, 24.7, 20.5. HRMS (TOF MS ES$^+$) calculated for $C_{20}H_{26}BN_2O_3S$ [MH]$^+$ requires 385.1757 found 385.1761.

tert-butyl 2-(4-oxo-2-((4-(4,4,5,5-tetramethyl-1,3,2-dioxaborolan-2-yl)benzyl)thio)-4,5,6,7-tetrahydro-1H-cyclopenta[d]pyrimidin-1-yl)acetate (6)

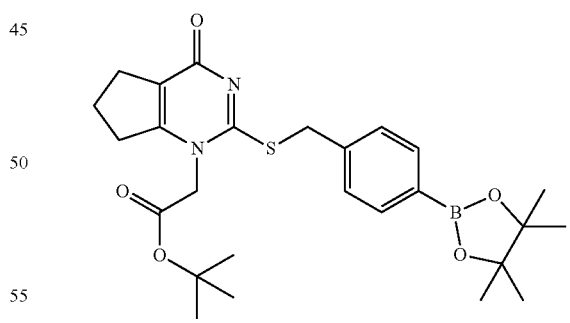

Compound 5 (1 eq, 3.72 mmol), DiPEA (1.2 eq, 4.47 mmol) and tert-butyl bromoacetate (1 eq, 3.72 mmol) were dissolved in dry DCM (21 mL) and stirred at 42° C. under argon for 20 h. The solution was poured into water (25 mL) and extracted with EtOAc 3 times (3×20 mL). The combined organic extracts were dried, filtered and evaporated under vacuum. The compound was purified using column chromatography (silica gel, 90/10 EtOAc/Hex) to obtain the desired compound (Rf=0.3) as a colourless solid (490 mg, 26%). $^1$H-NMR (600 MHz) δ: 7.59 (d, J=7.9 Hz, 2H), 7.41

(d, J=7.9 Hz, 2H), 4.67 (s, 2H), 4.46 (s, 2H), 2.81 (t, J=7.1 Hz, 2H), 2.58 (t, J=7.1 Hz, 2H), 1.97 (quint, J=7.1 Hz, 2H), 1.39 (s, 9H), 1.28 (s, 12H); $^{13}$C-NMR (600 MHz) δ: 165.9, 165.2, 160.3, 156.2, 140.2, 134.5, 128.6, 128.1, 119.7, 83.6, 82.9, 50.4, 35.2, 31.3, 27.9, 27.5, 24.6, 20.2. HRMS (TOF MS ES$^+$) calculated for $C_{27}H_{35}BN_2O_5S$ [MH]$^+$ requires 499.2438 found 499.2426.

2-((4-fluorobenzyl)thio)-1,5,6,7-tetrahydro-4H-cyclopenta[d]pyrimidin-4-one (2')

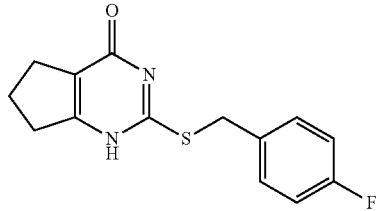 [SMILES: O=c1nc(SCc2ccc(F)cc2)[nH]c2c1CCC2]

Compound 4 (1 eq, 2.97 mmol), potassium carbonate (1.5 eq, 4.46 mmol) and potassium iodide (0.1 eq, 0.297 mmol) were stirred in acetone at rt. 4-fluorobenzyl chloride (1.05 eq, 3.12 mmol) was then added and the mixture was refluxed (ca 54° C.) for 1 h. An additional portion of potassium carbonate (0.2 eq, 0.59 mmol) was poured into the flask and the reflux was maintained for 2 h. After cooling with an ice bath to 0° C., the pH was adjusted to 1 using concentrated HCl. The reaction was stirred for 30 min until the precipitation was completed. The solid was then washed three times with water then dried at 55° C. overnight to afford the desired compound as a colourless solid (758 mg, 92%). $^1$H-NMR (DMSO-d6, 600 MHz) δ: 12.5 (bs, 1H), 7.46-7.43 (m, 2H), 7.15-7.12 (m, 2H), 4.37 (s, 2H), 2.76 (t, J=7.5 Hz, 2H), 2.58 (t, J=7.5 Hz, 2H), 1.96 (quint, J=7.5 Hz, 2H); $^{13}$C-NMR (DMSO-d6, 150 MHz) δ: 168.2, 166.2, 161.3 (d, $J_{CF}$=291 Hz), 159.3, 134.0 (m), 131.0 (d, $J_{CF}$=9 Hz), 119.9, 115.2 (d, $J_{CF}$=26 Hz), 34.3, 32.7, 26.7, 20.6.

tert-butyl 2-(2-((4-fluorobenzyl)thio)-4-oxo-4,5,6,7-tetrahydro-1H-cyclopenta[d]pyrimidin-1-yl)acetate (X)

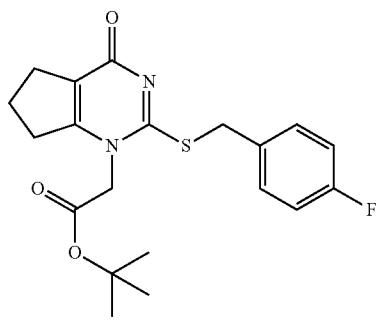 [SMILES: CC(C)(C)OC(=O)Cn1c(SCc2ccc(F)cc2)nc(=O)c2c1CCC2]

Compound 2' (1 eq, 0.73 mmol), DiPEA (1.2 eq, 0.87 mmol) and tert-butyl bromoacetate (1 eq, 0.73 mmol) were dissolved in dry DCM (10 mL) and stirred at 42° C. under argon for 20 h. The solution was poured on water and extracted with EtOAc (3×10 mL). The combined organic extracts were dried, filtered and evaporated under vacuum. The compound was purified using column chromatography (silica gel, 90/10 EtOAc/Hex) to afford the desired compound (Rf=0.2) as a colourless solid (47 mg, 21%). $^1$H-NMR (DMSO-d6, 600 MHz) δ: 7.32 (d, J=7.9 Hz, 2H), 7.01 (d, J=7.9 Hz, 2H), 4.51 (s, 2H), 4.31 (s, 2H), 2.68 (t, J=7.1 Hz, 2H), 2.50 (t, J=7.1 Hz, 2H), 1.88 (quint, J=7.1 Hz, 2H), 1.24 (s, 9H); $^{13}$C-NMR (CDCl$_3$, 150 MHz) δ: 165.8, 165.2, 161.4 (d, $J_{CF}$=291 Hz), 160.3, 156.2, 133.2 (d, $J_{CF}$=3 Hz), 131.1 (d, $J_{CF}$=11 Hz), 119.6, 115.2 (d, $J_{CF}$=26 Hz), 82.8, 50.4, 34.3, 31.3, 27.9, 27.5, 20.1;

2-(4-oxo-2-((4-(4,4,5,5-tetramethyl-1,3,2-dioxaborolan-2-yl)benzyl)thio)-4,5,6,7-tetrahydro-1H-cyclopenta[d]pyrimidin-1-yl)acetic acid (7)

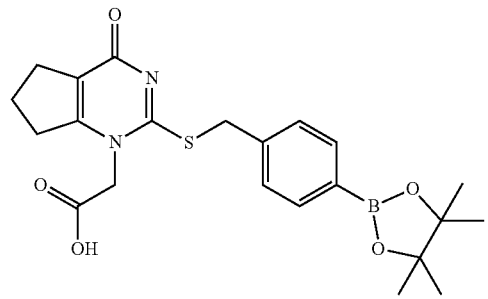 [SMILES: CC1(C)OB(c2ccc(CSc3nc(=O)c4c(n3CC(=O)O)CCC4)cc2)OC1(C)C]

Compound 6 (1 eq, 0.54 mmol) was dissolved in DCM (10 mL). TFA (40 eq, 21.7 mmol) was then added followed by slow addition of triisopropylsilane (2.5 eq, 1.35 mmol) at 0° C. The reaction mixture was stirred at rt under argon for 20 h. The clear solution was vacuumed to dryness and the compound was triturated in diethyl ether (5 mL) and dried to afford the desired compound as an off white solid (152 mg, 64%). $^1$H-NMR (DMSO-d$_6$) δ: 7.60 (d, J=8.0 Hz, 2H), 7.42 (d, J=8.0 Hz, 2H), 4.68 (s, 2H), 4.45 (s, 2H), 2.82 (t, J=7.2 Hz, 2H), 2.58 (t, J=7.2 Hz, 2H), 1.96 (quint, J=7.2 Hz, 2H), 1.28 (s, 12H); $^{13}$C-NMR (DMSO-d$_6$) δ: 168.2, 165.2, 160.3, 156.3, 140.1, 134.5, 128.6, 128.1, 119.6, 83.7, 49.9, 35.3, 31.2, 27.9, 24.6, 20.1. HRMS (TOF MS ES$^+$) calculated for $C_{22}H_{28}BN_2O_5S$ [MH]$^+$ requires 443.1812 found 443.1815.

4'-(trifluoromethyl)biphenyl-4-carbaldéhyde (18')

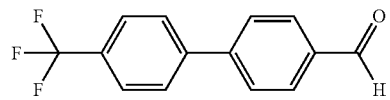 [SMILES: O=Cc1ccc(-c2ccc(C(F)(F)F)cc2)cc1]

Bromobenzaldehyde (1 eq, 0.95 mmol), 4-(Trifluoromethyl)phenylboronic acid (1.1 eq, 1.05 mmol), palladium (II) acetate, TBAB (1 eq, 0.95 mmol) and K$_2$CO$_3$ (2.5 eq, 2.37 mmol) were dissolved in a water/dioxane mixture (1/1 v/v) which was further deoxygenated three times (vacuum/ar). Palladium (II) acetate (0.05 eq, 0.05 mmol) was then added to the resulting solution and the reaction mixture was heated to 70° C. under stirring and argon for 3 h until reaction completion was shown by TLC. Water was added followed by extraction with EtOAc (3×10 mL). The combined organic phases were washed with brine then dried and filtered. After removal of the solvent under reduced pressure, the remaining paste was purified using column chromatography (silica gel, 95/5 hexane/EtOAc) to afford the desired compound (Rf=0.35) as a colourless solid (210 mg, 89%).

$^{1}$H-NMR (CDCl$_3$, 600 MHz) δ 10.09 (s, 1H), 7.99 (m, 2H), 7.77 (m, 2H), 7.74 (m, 4H); $^{13}$C-NMR (CDCl$_3$, 150 MHz) δ 191.7, 145.6, 143.3, 135.9, 130.6 (m), 130.4, 128.0, 127.7, 126.0 (m), 125.9 (m);

N1,N1-diethyl-N2-((4'-(trifluoromethyl)biphenyl-4-yl)methyl)ethane-1,2-diamine (8)

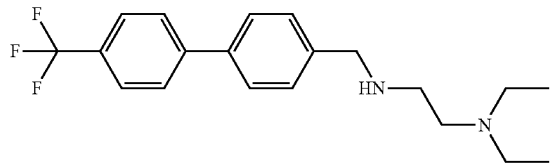 [SMILES: CCN(CC)CCNCc1ccc(-c2ccc(C(F)(F)F)cc2)cc1]

Compound 18' (1 eq, 1.01 mmol) and N,N-diethylethylenediamine (1.05 eq, 1.05 mmol) were dissolved in DCM (5 mL) at rt under argon. The resulting clear solution was stirred during 1 h followed by addition of NaBH(OAc)$_3$ (1.4 eq, 1.40 mmol) at 0° C. The reaction mixture was then stirred at rt for 3 h until TLC showed reaction completion. Quenching with NaOH was followed by extraction using DCM (3×15 mL). The combined organic phases were washed with brine then dried and filtered. After removal of the solvent under reduced pressure, the remaining orange oil was purified using column chromatography (silica gel, 85/15 DCM/MeOH) to afford the desired compound (Rf=0.25) as a yellow oil (310 mg, 80%).

$^{1}$H-NMR (CDCl$_3$, 600 MHz) δ 7.68 (s, 4H), 7.57 (d, J=8.1 Hz, 2H), 7.43 (d, J=8.1 Hz, 2H), 3.87 (s, 2H), 2.74 (t, J=6.1 Hz, 2H), 2.63 (t, J=6.1 Hz, 2H), 2.57 (q, J=7.1 Hz, 4H), 1.05 (t, J=7.1 Hz, 6H);

$^{13}$C-NMR (CDCl$_3$, 150 MHz) δ 144.6, 140.3, 138.6, 129.4 (m), 129.0, 127.4, 127.3, 125.8 (m), 124.5 (m), 53.6, 52.5, 47.2, 46.3, 11.3; ESI-MS m/z for C$_{20}$H$_{25}$F$_3$N$_2$ [MH]$^+$ 351.4, [MNa]$^+$ 373.8;

N-(2-(diethylamino)ethyl)-2-(4-oxo-2-((4-(4,4,5,5-tetramethyl-1,3,2-dioxaborolan-2-yl)benzyl)thio)-4,5,6,7-tetrahydro-1H-cyclopenta[d]pyrimidin-1-yl)-N-((4'-(trifluoromethyl)-[1,1'-biphenyl]-4-yl)methyl)acetamide (9)

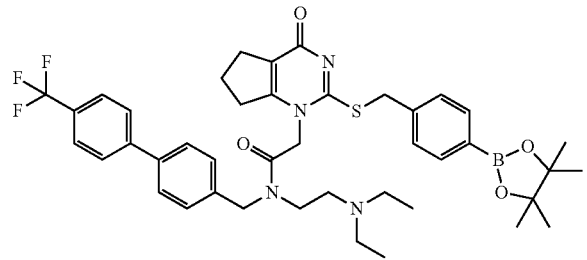 [SMILES: CCN(CC)CCN(Cc1ccc(-c2ccc(C(F)(F)F)cc2)cc1)C(=O)Cn1c(SCc2ccc(B3OC(C)(C)C(C)(C)O3)cc2)nc(=O)c2c1CCC2]

Compound 8 (1 eq, 0.11 mmol) and 7 (1 eq, 0.11 mmol) were dissolved in DMF (1.5 mL) then stirred with DIPEA (2 eq, 0.22 mmol) for 10 min at rt. The reaction was then cooled with an ice bath to 0° C. and COMU (1 eq, 0.11 mmol) was added portionwise. The mixture was stirred at 0° C. for 1 h then the bath was removed and the reaction was allowed to reach rt and was continued for 12 h. The compound was extracted using EtOAc 3 times (3×5 mL). The combined organic layers were then washed several times with saturated NaHCO$_3$ until the washing solution was colourless. The resulting organic solution was dried, filtered and evaporated under vacuum. The remaining paste was purified using column chromatography (silica gel, 90/10 DCM/MeOH) to afford the desired compound (Rf=0.35) as a light yellow solid (60 mg, 70%). $^{1}$H-NMR (CDCl$_3$) Mix of rotamers ratio (0.85/0.15) δ 7.89-7.72 (m, 5H), 7.69-7.66 (m, 3H), 7.45-7.30 (m, 4H), 5.13 (s, 1.3H), 4.87 (m, 0.7H), 4.73 (s, 0.7H), 4.62 (s, 1.3H), 4.46 (m, 0.7H), 4.44-4.34 (m, 1.3H), 3.48-3.45 (m, 0.3H), 3.44-3.38 (m, 1.7H), 2.79-2.71 (m, 2H), 2.62-2.72 (m, 4H), 2.77-2.75 (m, 4H), 2.45-2.41 (m, 2H), 2.00-1.93 (m, 2H), 1.26 (s, 4H), 1.23 (s, 8H), 0.89 (t, J=7.1 Hz, 4H), 0.84 (t, J=7.1 Hz, 2H); $^{13}$C-NMR (CDCl$_3$) Mix of rotamers ratio (0.85/0.15) δ 167.8, 167.8, 167.6, 167.5, 162.7, 162.5, 145.8, 145.7, 140.0, 139.4, 136.6, 136.3, 130.7, 130.6, 130.3, 130.2, 129.6, 129.3 (m), 129.0, 127.8 (m), 121.5 (m), 118.2, 115.5, 85.6, 71.8, 60.9, 52.4, 52.0, 50.3, 50.1, 48.9, 48.7, 37.4, 31.0, 30.0, 26.4, 22.1, 13.6. HRMS (TOF MS ES$^+$) calculated for C$_{42}$H$_{51}$BF$_3$N$_4$O$_4$S [MH]$^+$ requires 775.3676 found 775.3690.

Darapladib (10)

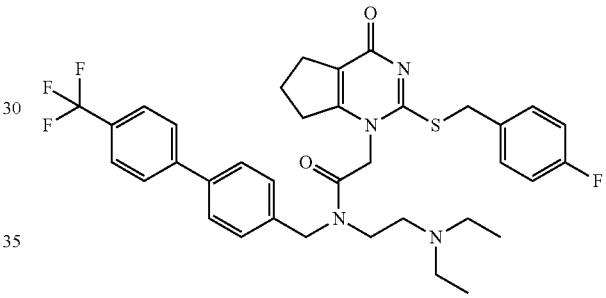

Amine 8 (1 eq, 52 mg) and acid 12' (1 eq, 50 mg) were dissolved in DMF (1 mL) then stirred with DIPEA (2 eq, 52 µL) for 10 min at rt. The reaction was then cooled with an ice bath to 0° C. and COMU (1 eq, 64 mg) was added. The mixture was stirred at 0° C. for 1 h then the bath was removed and the reaction was allowed to reach rt and continued for 5 h. The compound was extracted using EtOAc three times (5 mL×3). The combined organic layers were then washed several times with saturated NaHCO$_3$ until washing solution was colourless. The resulting organic solution was dried, filtered and evaporated. The product was then purified using column chromatography on silica gel DCM/MeOH (90/10) (Rf=0.2) as a pale yellow solid (65 mg, 65%). $^{1}$H NMR (600 MHz, CDCl$_3$) Mix of rotamers ratio (1/1) δ 7.69 (d, J=7.9 Hz, 2H), 7.62 (d, J=7.9 Hz, 1H), 7.56 (d, J=6.7 Hz, 1H), 7.46 (m, 2H), 7.37-7.26 (m, 4H), 6.96 (t, J=7.4 Hz, 1H), 6.89 (t, J=7.4 Hz, 1H), 4.95 (s, 1H), 4.69 (m, 3H), 4.50 (s, 1H), 4.40 (s, 1H), 3.64 (m, 1H), 3.30 (m, 1H), 2.88 (m, 1H), 2.81 (t, J=6.7 Hz, 1H), 2.76 (t, J=6.7 Hz, 4H), 2.59 (t, J=7.1 Hz, 2H), 2.51 (q, J=7.0 Hz, 2H), 2.11 (quint, J=7.4 Hz, 1H), 2.05 (quint, J=7.4 Hz, 1H), 1.10 (t, J=7.1 Hz, 3H), 0.98 (t, J=7.1 Hz, 3H).

$^{13}$C-NMR (CDCl$_3$, 150 MHz) Mix of rotamers δ: 167.5, 166.5, 162.2 (d, J$_{CF}$=240 Hz), 161.4, 161.3, 156.8, 156.5, 144.1, 143.6, 139.8, 139.3, 136.8, 135.4, 131.5 (d, J$_{CF}$=3 Hz), 131.2 (d, J$_{CF}$=9 Hz), 131.1 (d, J$_{CF}$=3 Hz), 129.8 (m), 128.8, 128.0 (m), 127.7 (m), 127.4, 127.3, 127.2, 125.9 (m), 124.4 (m), 121.3, 121.2, 115.7 (d, J$_{CF}$=23 Hz), 115.6 (d, J$_{CF}$=23 Hz), 51.4, 50.4, 50.3, 50.1, 49.2, 47.8, 47.3, 46.1, 36.6, 36.5, 32.1, 32.0, 28.5, 28.4, 20.9, 20.8, 11.8;

1.4. Synthesis of Radiolabelling Precursors 11
Scheme 3
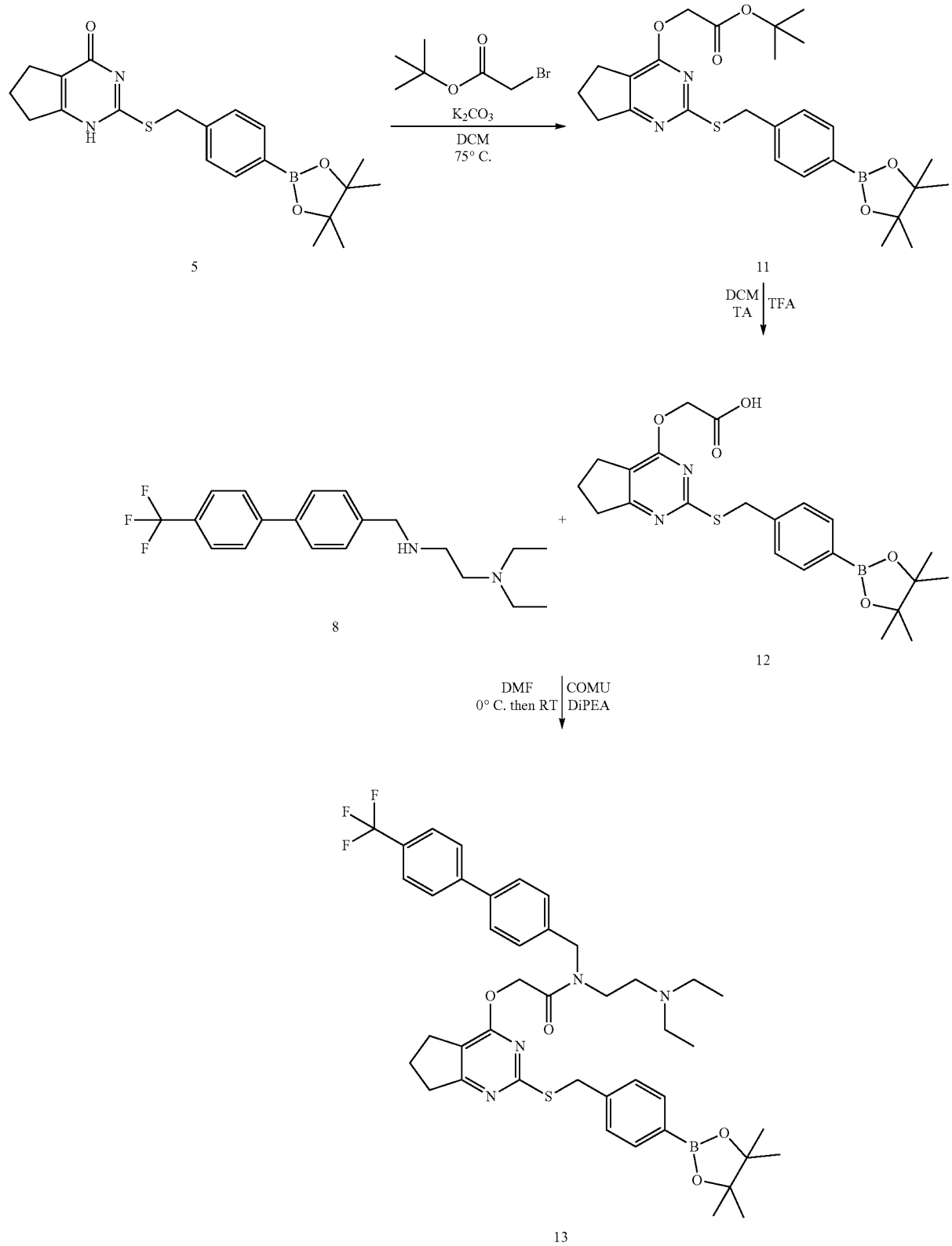

tert-butyl 2-(4-oxo-2-((4-(4,4,5,5-tetramethyl-1,3,2-dioxaborolan-2-yl)benzyl)thio)-4,5,6,7-tetrahydro-1H-cyclopenta[d]pyrimidin-1-yl)acetate (11)

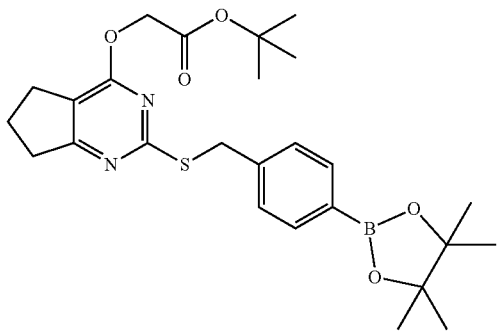 [SMILES: CC(C)(C)OC(=O)COc1nc(SCc2ccc(B3OC(C)(C)C(C)(C)O3)cc2)nc2c1CCC2]

Compound 5 (1 eq, 1.40 mmol), potassium carbonate (1.2 eq, 1.68 mmol) and tert-butyl bromoacetate (1.2 eq, 1.68 mmol) were dissolved in dry DMF (15 mL) and stirred at 75° C. under argon for 18 h. The reaction was monitored by TLC and the mixture was then dried under vacuum when it was deemed completed. The compound was purified using column chromatography (silica gel, 90/10 Hex/EtOAc) to afford the desired compound (Rf=0.3) as a colorless oil (654 mg, 94%). $^1$H-NMR (DMSO-$d_6$, 600 MHz) δ 7.59 (d, J=7.9 Hz, 2H), 7.39 (d, J=7.9 Hz, 2H), 4.78 (s, 2H), 4.34 (s, 2H), 2.83 (t, J=7.1 Hz, 2H), 2.73 (t, J=7.1 Hz, 2H), 2.03 (quint, J=7.1 Hz, 2H), 1.36 (s, 9H), 1.26 (s, 12H); $^{13}$C-NMR (DMSO-$d_6$, 150 MHz) δ 176.2, 167.6, 167.2, 164.0, 141.4, 134.6, 128.3, 115.1, 83.7, 81.5, 62.9, 59.8, 34.3, 33.5, 27.7, 25.7, 24.7, 21.5. HRMS (TOF MS ES$^+$) calculated for $C_{26}H_{36}BN_2O_5S$ [MH]$^+$ requires 499.2438 found 499.2438.

2-((2-((4-(4,4,5,5-tetramethyl-1,3,2-dioxaborolan-2-yl)benzyl)thio)-6,7-dihydro-5H-cyclopenta[d]pyrimidin-4-yl)oxy)acetic acid (12)

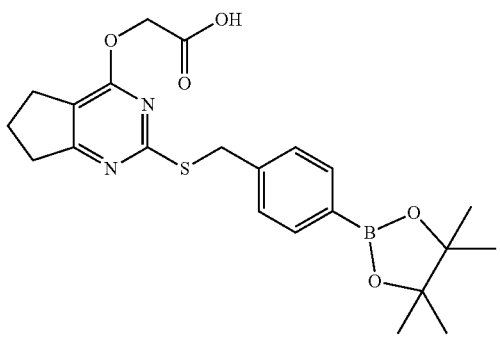 [SMILES: CC1(C)OB(c2ccc(CSc3nc4c(c(OCC(=O)O)n3)CCC4)cc2)OC1(C)C]

Compound 11 (1 eq, 1.31 mmol) was dissolved in DCM (5 mL). TFA (12 eq, 15.72 mmol) was then added and the reaction mixture was stirred at rt under argon for 18 h. The clear solution was vacuumed to dryness and the compound was purified using column chromatography (silica gel, 40/60 Hex/EtOAc) to afford the desired compound (Rf=0.2) as an off white solid (426 mg, 74%). $^1$H-NMR (DMSO-$d_6$, 600 MHz) δ 7.59 (d, J=7.7 Hz, 2H), 7.39 (d, J=7.7 Hz, 2H), 4.87 (s, 2H), 4.33 (s, 2H), 2.82 (t, J=6.4 Hz, 2H), 2.74 (t, J=6.4 Hz, 2H), 2.03 (quint, J=6.4 Hz, 2H), 1.26 (s, 12H); $^{13}$C-NMR (DMSO-$d_6$, 150 MHz) δ 176.2, 179.6, 167.6, 164.1, 141.6, 134.6, 134.5, 118.5, 115.1, 83.7, 62.4, 34.2, 33.5, 25.7, 24.7, 21.5. HRMS (TOF MS ES$^+$) calculated for $C_{22}H_{28}BN_2O_5S$ [MH]$^+$ requires 443.1812 found 443.1797.

N-(2-(diethylamino)ethyl)-2-((2-((4-(4,4,5,5-tetramethyl-1,3,2-dioxaborolan-2-yl)benzyl)thio)-6,7-dihydro-5H-cyclopenta[d]pyrimidin-4-yl)oxy)-N-((4'-(trifluoromethyl)-[1,1'-biphenyl]-4-yl)methyl)acetamide (13)

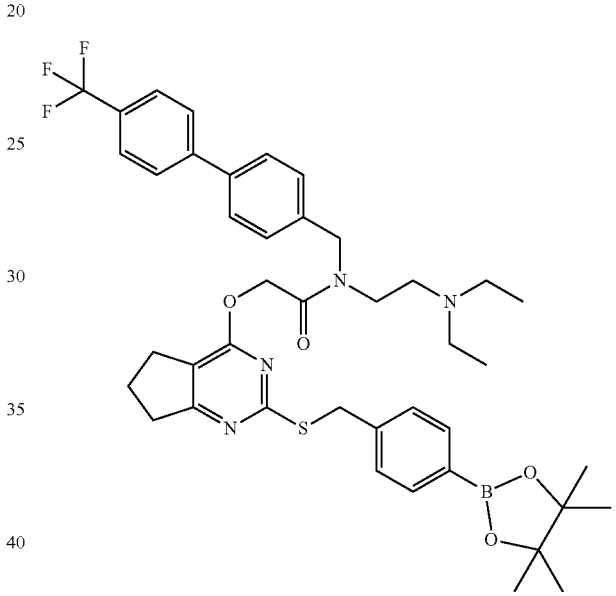

Compound 12 (1 eq, 0.23 mmol) and 8 (1 eq, 0.23 mmol) were dissolved in DMF (2 mL) then stirred with DIPEA (2 eq, 0.46 mmol) for 10 min at rt. The reaction was then cooled with an ice bath to 0° C. and COMU (1 eq, 0.23 mmol) was added portionwise. The mixture was stirred at 0° C. for 1 h then the bath was removed and the reaction was allowed to reach rt and continued for 5 h. The compound was extracted using EtOAc 3 times (3×5 mL). The combined organic layers were then washed several times with saturated NaHCO$_3$ until the washing solution was colourless. The resulting organic solution was dried, filtered and evaporated under vacuum. The remaining paste was purified using column chromatography (silica gel, 90/10 AE/MeOH) to afford the desired compound (Rf=0.3) as an off white solid (115 mg, 65%). $^1$H-NMR (DMSO-$d_6$, 600 MHz) Mix of rotamers ratio (1/1) δ 7.75 (d, J=7.9 Hz, 1H), 7.71 (d, J=7.9 Hz, 1H), 7.68 (m, J=6.7 Hz, 2H), 7.59 (m, 2H), 7.56 (d, J=8.1 Hz, 1H), 7.51 (d, J=8.1 Hz, 1H), 7.42 (d, J=7.9 Hz, 1H), 7.37 (d, J=7.9 Hz, 1H), 7.34 (d, J=7.4 Hz, 2H), 5.14 (s, 1H), 5.06 (s, 1H), 4.67 (s, 1H), 4.63 (s, 1H), 4.38 (s, 1H), 4.32 (s, 1H), 3.69 (m, 1H), 3.50 (t, J=6.7 Hz, 2H), 3.30 (t, J=6.7 Hz, 1H), 3.23 (m, 1H), 2.90 (m, 2H), 2.88 (m, 2H), 2.80 (t, J=7.4 Hz, 1H), 2.76 (t, J=6.7 Hz, 1H), 2.64 (m, 2H), 2.57 (t, J=6.7 Hz, 1H), 2.11 (quint, J=7.4 Hz, 1H), 2.06

(quint, J=7.4 Hz, 1H), 1.33 (s, 6H), 1.32 (s, 6H), 1.03 (t, J=7.1 Hz, 3H), 0.98 (t, J=7.1 Hz, 3H); $^{13}$C-NMR (DMSO-d$_6$, 150 MHz) δ Mix of rotamers ratio (1/1) δ 176.3, 176.2, 168.8, 167.9, 164.7, 164.5, 144.3, 143.9, 141.0, 140.9, 139.4, 138.9, 137.5, 136.7, 135.1 (2C, 135.0, 129.8, 129.7, 129.6, 129.5, 128.7, 128.5, 128.4, 128.0, 127.7, 127.5, 127.4, 127.3, 125.9-125.8, 115.8, 115.7, 84.0, 83.9, 63.3, 62.9, 51.7, 51.3, 49.1, 47.6, 47.7, 47.4, 45.7, 44.9, 35.6, 34.3, 34.2, 26.4, 26.3, 25.0, 22.0, 21.9, 12.0; HRMS (TOF MS ES$^+$) calculated for $C_{42}H_{51}BF_3N_4O_4S$ [MH]$^+$ requires 775.3676 found 775.3686.

1.5 Synthesis ter-butyl 2-(2-((4-fluorobenzyl)thio)-4-oxo-4,5,6,7-tetrahydro-1H-cyclopenta[d]pyrimidin-1-yl)acetate (3')

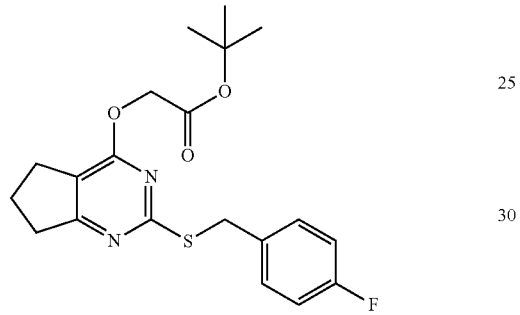

Compound 2' (1 eq, 1.40 mmol), potassium carbonate (1.2 eq, 1.68 mmol) and tert-butyl bromoacetate (1.2 eq, 1.68 mmol) were dissolved in dry DMF (2 mL) and stirred at 75° C. under argon for 18 h. The reaction was monitored by TLC and the mixture was then dried under vacuum when it was deemed completed. The compound was purified using column chromatography (silica gel, 90/10 Hex/EtOAc) to afford the desired compound (Rf=0.3) as a colorless oil (654 mg, 94%).

$^1$H-NMR (CDCl$_3$, 600 MHz) δ 7.44 (d, J=7.9 Hz, 2H), 7.14 (d, J=7.9 Hz, 2H), 4.82 (s, 2H), 4.34 (s, 2H), 2.86 (t, J=7.1 Hz, 2H), 2.76 (t, J=7.1 Hz, 2H), 2.06 (quint, J=7.1 Hz, 2H), 1.38 (s, 9H);

$^{13}$C-NMR (CDCl$_3$, 150 MHz) δ: 176.2, 167.6, 167.2, 164.0, 161.2 (d, J$_{CF}$=243 Hz), 134.0 (m), 130.6 (d, J$_{CF}$=9 Hz), 115.2 (d, J$_{CF}$=21 Hz), 115.1, 81.5, 62.9, 33.5, 33.4, 27.7, 25.7, 21.5;

HRMS (ESI) calculated for $C_{26}H_{35}BN_2O_5S$ [MH]$^+$ requires 498,2360, found

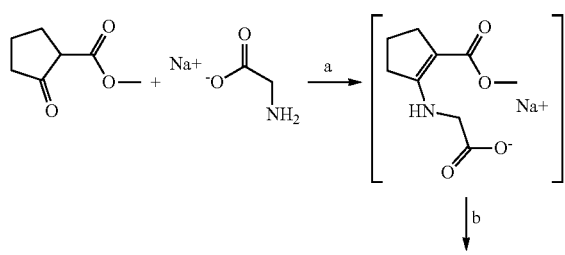

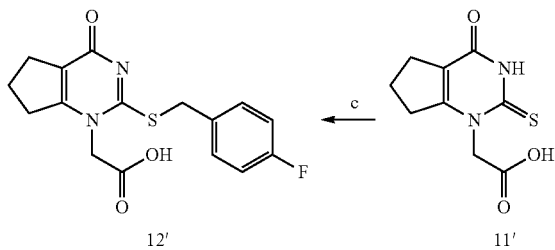

Reagents and conditions: (a) NMP, 60° C.; (b) NaSCN, TMSCl, 120° C., 58%; (c) 4-fluorobenzyl chloride, KOH, K$_2$CO$_3$, H2O/IPA, 40° C., 60%.

2-(4-oxo-2-thioxo-2,3,4,5,6,7-hexahydro-1H-cyclopenta[d]pyrimidin-1-yl)acetic acid (11')

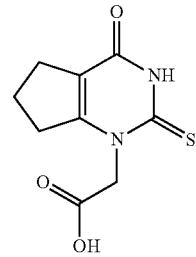 [SMILES: O=C(O)Cn1c2c(c(=O)[nH]c1=S)CCC2]

Methyl 2-oxocyclopentanecarboxylate (1 eq, 17.5 mmol) was added to a stirred suspension of glycine sodium salt (1 eq, 18.0 mmol) in NMP (18 mL). The reaction mixture was stirred for 2 hours at 60° C. under argon atmosphere. After cooling the mixture to room temperature, sodium thiocyanate (1.4 eq, 25 mmol) was added. Chlorotrimethylsilane (3.5 eq, 61.5 mmol) was then added dropwise and the reaction mixture was stirred at 120° C. for 3 hours. The reaction was cooled to 90° C. and water (35 mL) was added. The resulting suspension was slowly cooled to 4° C. overnight and the product was collected by filtration. The product was washed with water (2×15 mL) and acetone (15 mL) then dried at 50° C. to yield the title compound as an off white solid (1.4 g, 58%).

$^1$H-NMR (DMSO-d6, 600 MHz) δ 12.55 (s, 1H), 4.92 (bs, 2H), 2.85 (m, 2H), 2.58 (m, 2H) 1.98 (m, 2H);

$^{13}$C-NMR (DMSO-d6, 150 MHz) δ 177.0, 168.5, 158.4, 157.8, 117.0, 51.6, 32.7, 27.5, 20.5; ESI-MS m/z for $C_9H_{10}N_2O_3S$ [MH]$^+$, [MNa]$^+$ 191.4;

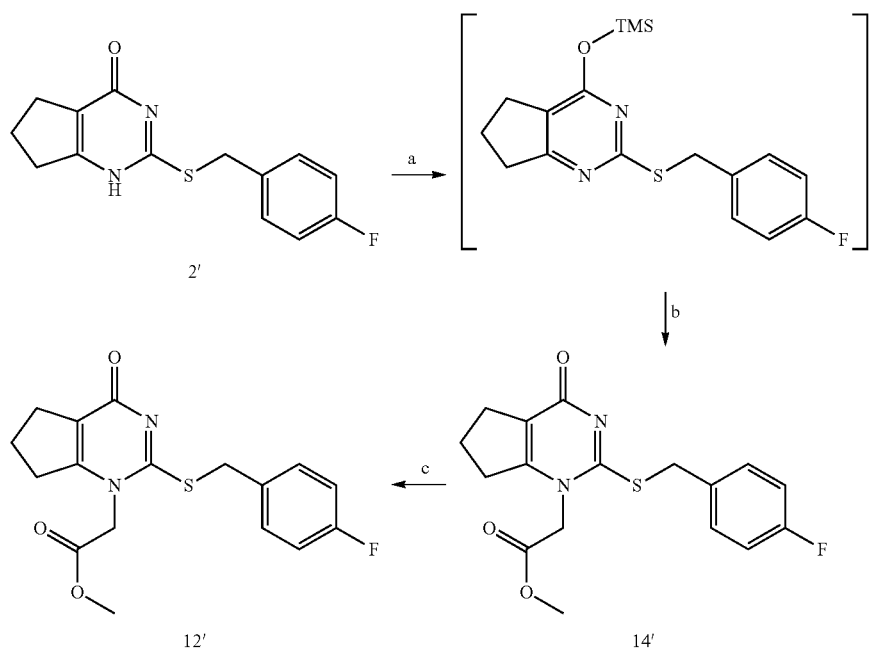

Reagents and conditions: (a) saccharin, HMDS, DCM, reflux; (b) (trifluoromethanesulfonyloxy)-acetic acid methyl ester, DCM, reflux; (c) NaOH 10% (w/v), IPA then HCl (5 M).

2-2-(4-flurobenzylthio)-4-oxo-4,5,6,7-tetrahydro-1H-cyclopenta[d]pyrimidin-1-yl)acetic acid (12')

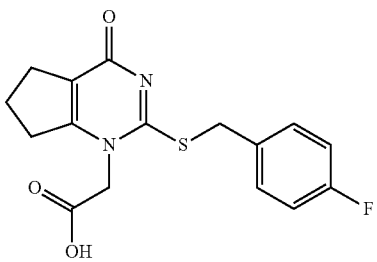 [SMILES: O=C(O)Cn1c(SCc2ccc(F)cc2)nc(=O)c2c1CCC2]

Compound 11' (1 eq, 1.62 mmol) was stirred in a mixture of water (3 mL) and isopropyl alcohol (820 µL). KOH aqueous solution (50% w/v, 1.9 eq, 3.08 mmol) was added followed by K$_2$CO$_3$ (0.15 eq, 0.24 mmol) and the reaction was heated to 40° C. under constant stirring. 4-fluorobenzyl chloride (0.95 eq, 1.52 mmol) was then added and the reaction was stirred at 40° C. for 3 hours. The reaction was cooled to room temperature and formic acid (0.5 eq, 0.8 mmol) was added to crystallize the product. After 1 h, more formic acid (1.7 eq, 2.7 mmol) was slowly added and the reaction was stirred for at least an hour until crystallization was complete. The product was collected through filtration and washed twice with a 4:1 (v:v) mixture of water and isopropyl alcohol (1 mL) followed by isopropyl alcohol (1 mL). The product was stirred in ether overnight to remove remaining organic impurities and filtered again. Product was dried at 50° C. to afford the title compound as a colourless solid (300 mg, 60%).

M.p. 183-185° C.

1H-NMR (CDCl$_3$, 600 MHz) δ 12.54 (s, 1H), 7.45 (dd, J=8.6, 5.6, 2H), 7.11 (t, J=8.6, 2H), 4.63 (s, 2H), 4.43 (s, 2H), 2.82 (t, J=7.3, 2H), 2.59 (t, J=7.3, 2H), 1.97 (q, J=7.3, 2H);

$^{13}$C-NMR (CDCl$_3$, 150 MHz) δ: 168.3, 165.7, 161.6 (d, J$_{CF}$=240 Hz), 156.7, 133.2 (d, J$_{CF}$=3 Hz), 131.3 (d, J$_{CF}$=7.5 Hz), 119.8, 115.3 (d, J$_{CF}$=21 Hz), 50.1, 34.6, 31.4, 28.0, 20.2;

ter-butyl 2-(2-((4-fluorobenzyl)thio)-4-oxo-4,5,6,7-tetrahydro-3H-cyclopenta[d]pyrimidin-3-yl)-acetate (13')

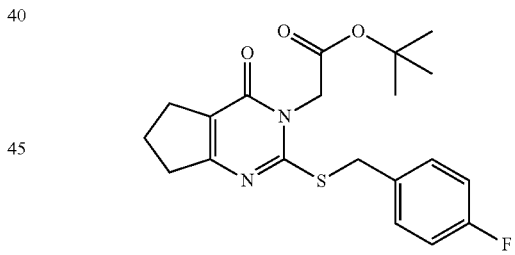

Compound 2' (1 eq, 0.73 mmol), DiPEA (1.2 eq, 0.87 mmol) and tert-butyl bromoacetate (1 eq, 0.73 mmol) were dissolved in dry DCM (6 mL) and stirred at 42° C. under argon for 20 h. The solution was poured on water and extracted with EtOAc (3×15 mL). The combined organic extracts were dried, filtered and evaporated under vacuum. The compound was purified using column chromatography (silica gel, 90/10 Hex/EtOAc) to obtain the desired compound (Rf=0.3) as a colourless solid (76 mg, 27%).

$^1$H NMR (600 MHz, DMSO-d$_6$) δ: 7.46 (d, J=7.9 Hz, 2H), 7.14 (d, J=7.9 Hz, 2H), 4.65 (s, 2H), 4.46 (s, 2H), 2.82 (t, J=7.1 Hz, 2H), 2.64 (t, J=7.1 Hz, 2H), 2.02 (quint, J=7.1 Hz, 2H), 1.30 (s, 9H).

$^{13}$C-NMR (150 MHz, DMSO-d$_6$) δ: 167.0, 165.8, 161.5 (d, J$_{CF}$=291 Hz), 160.6, 159.0, 132.8 (d, J$_{CF}$=3 Hz), 131.3 (d, J$_{CF}$=11 Hz), 118.4, 115.2 (d, J$_{CF}$=26 Hz), 82.3, 45.0, 34.7, 34.3, 27.5, 27.2, 20.8;

methyl 2-(2-((4-fluorobenzyl)thio)-4-oxo-4,5,6,7-tetrahydro-1H-cyclopenta[d]pyrimidin-1-yl)acetate (14')

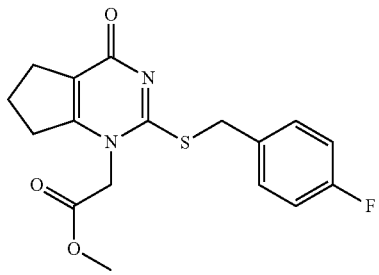 [SMILES: COC(=O)Cn1c(SCc2ccc(F)cc2)nc(=O)c2c1CCC2]

Compound 2' (1 eq, 0.90 mmol), saccharin (0.01 eq, 0.009 mmol) were dissolved in DCM (5 mL) and stirred at 42° C. HMDS (0.6 eq, 0.54 mmol) was slowly added and the mixture was stirred at reflux for 1 h 30. (trifluoromethanesulfonyloxy)-acetic acid methyl ester (1.5 eq, 1.35 mmol) dissolved in 500 µL of DCM was slowly added over 10 min. The resulting clear solution was stirred at 42° C. for 10 h. 5 mL of HCl 1N was added followed by water (5 mL). The aqueous phase was extracted 3 times with EtOAc (5 mL). The combined organic extracts were washed with saturated NaHCO$_3$ (10 mL) then brine (10 mL). The organic layer was dried, filtered and solvents were removed under reduced pressure. The resulting paste was purified using column chromatography (silica gel, 95/5, EtOAc/MeOH) to obtain the desired compound as a colourless solid (291 mg, 93%).

$^1$H-NMR (DMSO-d6, 600 MHz) δ 7.46 (d, J=7.9 Hz, 2H), 7.14 (d, J=7.9 Hz, 2H), 4.80 (s, 2H), 4.42 (s, 2H), 3.70 (s, 3H), 2.83 (t, J=7.1 Hz, 2H), 2.58 (t, J=7.1 Hz, 2H), 1.97 (quint, J=7.1 Hz, 2H);

$^{13}$C-NMR (600 MHz, DMSO-d$_6$) δ: 170.9, 167.4, 165.4, 164.4, 161.4 (d, J$_{CF}$=207 Hz), 130.9 (d, J$_{CF}$=8 Hz), 130.6 (d, J$_{CF}$=3 Hz), 120.0, 115.6 (d, J$_{CF}$=23 Hz), 65.0, 53.4, 36.0, 32.7, 26.9, 21.2;

Methyl 2-((2-((4-fluorobenzyl)thio)-6,7-dihydro-5H-cyclopenta[d]pyrimidin-4-yl)-oxy)acetate (15')

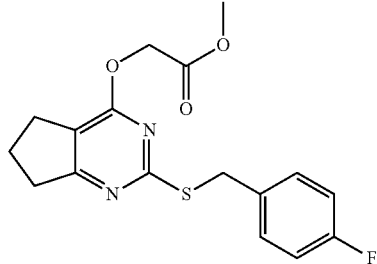 [SMILES: COC(=O)COc1nc(SCc2ccc(F)cc2)nc2c1CCC2]

Compound 2' (1 eq, 0.18 mmol), potassium carbonate (1.2 eq, 0.22 mmol) and tert-butyl 2-(tosyloxy)acetate (1.2 eq, 0.22 mmol) were dissolved in dry DMF (14 mL) and stirred at 75° C. under argon for 18 h. The reaction was monitored by TLC and the mixture was then dried under vacuum when it was deemed completed. The compound was purified using column chromatography (silica gel, 90/10 Hex/EtOAc) to obtain the desired compound (Rf=0.3) as a colorless oil (48 mg, 58%).

$^1$H-NMR (DMSO-d6, 600 MHz) δ 7.41 (d, J=7.9 Hz, 2H), 7.13 (d, J=7.9 Hz, 2H), 4.98 (s, 2H), 4.31 (s, 2H), 3.63 (s, 3H), 2.85 (t, J=7.1 Hz, 2H), 2.77 (t, J=7.1 Hz, 2H), 2.01 (quint, J=7.1 Hz, 2H);

$^{13}$C-NMR (150 MHz, DMSO-d$_6$) δ: 176.9, 169.1, 168.2, 164.4, 161.2 (d, J$_{CF}$=194 Hz), 134.3 (d, J$_{CF}$=5 Hz), 131.0 (d, J$_{CF}$=9 Hz), 115.6 (d, J$_{CF}$=21 Hz), 115.5, 62.9, 52.4, 33.9, 33.8, 26.2, 21.9;

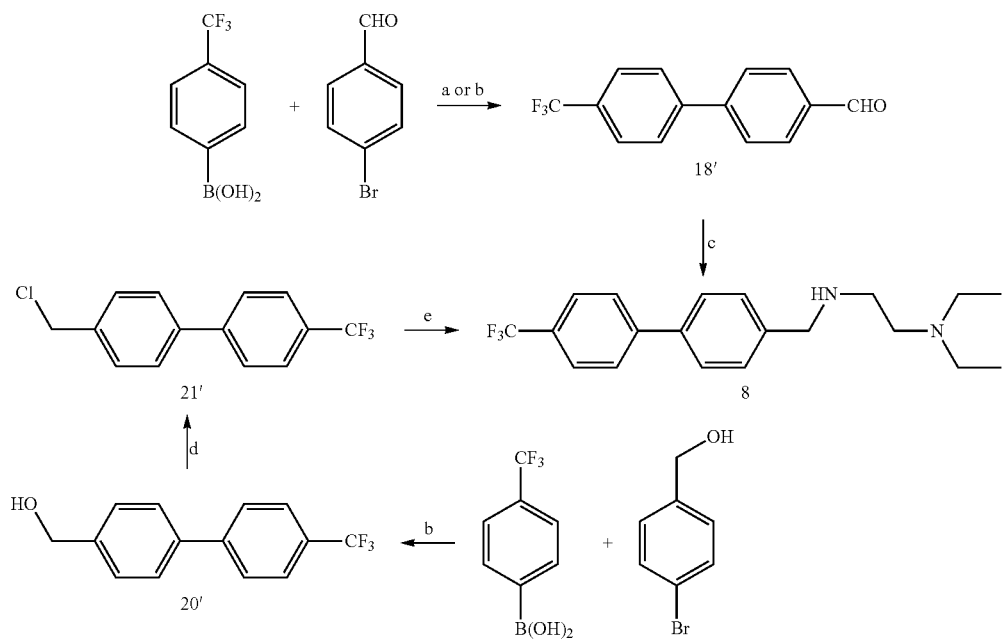

Reagents and conditions:
(a) Pd(OAc)$_2$, TBAB, K$_2$CO$_3$, dioxane/water, 70° C., 89%;
(b) Pd(OAc)$_2$, TBAB, Na$_2$CO$_3$, water, 150° C., 98% (12), 93% (13);
(c) NaBH(OAc)$_3$, N,N-Diethylethylenediamine, DCM, 0° C. then RT, 80%;
(d) SOCl$_2$, DMF (cat), DCM, 0° C. then RT, 91%;
(e) K$_2$CO$_3$, DMF, 70° C., 94%.

(4'-(trifluoromethyl)-[1,1'-biphenyl]-4-yl)methanol (20')

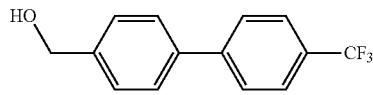

Compound 1 (1 eq, 5.35 mmol), 4-(Trifluoromethyl) phenylboronic acid (1 eq, 5.35 mmol), TBAB (1 eq, 5.35 mmol), $Na_2CO_3$ (3 eq, 16.05 mmol) were dissolved in 11 mL of water. Palladium acetate (0.4% eq, 0.021 mmol) was then added and the reaction was stirred in a scelled tube and heated at 150° C. After 20 min, the tube is slowly cooled down to rt and opened with caution. The biphase mixture is poured onto 10 mL of EtOAc and extracted (3×10 mL). The combined organic phases were dried and filtered. After removal of the solvent under reduced pressure, the remaining black oil was purified using column chromatography (silica gel, 80/20 Hex/EtOAc) to afford the desired compound (Rf=0.2) as a colourless solid (1.29 g, 96%).

$^1$H-NMR (CDCl$_3$, 600 MHz) δ 7.69 (s, 4H), 7.60 (d, J=8.1 Hz, 2H), 7.47 (d, J=8.1 Hz, 2H), 4.77 (s, 2H);
$^{13}$C-NMR (CDCl$_3$, 150 MHz) δ: 144.5, 141.1, 139.3, 129.1, 127.7, 127.6, 127.5, 125.9, 124.4, 65.1; ESI-MS m/z for $C_{14}H_{11}F_3O$ [MH]$^+$, [MNa]$^+$;

4-(chloromethyl)-4'-(trifluoromethyl)-1,1'-biphenyl (21')

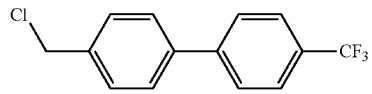 [SMILES: FC(F)(F)c1ccc(-c2ccc(CCl)cc2)cc1]

Compound 20' (1 eq, 9.51 mmol) was dissolved in 20 mL of CHCl$_3$. SOCl$_2$ (2 eq, 19.0 mmol) was then added and the reaction was stirred at rt during 12 h. The reaction mixture was evaporated to dryness and diluted with water (30 mL) and EtOAc (40 mL). The mixture was then extracted three times (3×20 mL). The combined organic phases were washed with saturated $Na_2CO_3$, dried and filtered. After removal of the solvent under reduced pressure, the remaining oil was purified using column chromatography (silica gel, 98/2 Hex/EtOAc) to obtain the desired compound (Rf=0.2) as an off white solid (2.35 g, 91%)

$^1$H-NMR (CDCl$_3$, 600 MHz) δ 7.69 (s, 4H), 7.59 (d, J=8.1 Hz, 2H), 7.49 (d, J=8.1 Hz, 2H), 4.64 (s, 2H);
$^{13}$C-NMR (CDCl$_3$, 150 MHz) δ: 144.2, 140.0, 137.6, 129.8, 129.4, 127.8, 127.6, 125.9, 120.3, 45.9;
ESI-MS m/z for $C_{14}H_{11}F_3O$ [M+H]$^+$, [M+Na]$^+$;

2. Radiochemistry

2.1. General Materials and Methods

All reagents were purchased from commercial suppliers and used without further purification (Acros and Sigma-Aldrich).

Radioisotope Production.

No-carrier-added fluorine-18 (half-life: 109.8 min) was produced via the [$^{18}$O(p,n)$^{18}$F] nuclear reaction by irradiation of a 1.5 ml [$^{18}$O]water (IBA CisBio) target with an 16.5 MeV proton beam on a cyclotron General Electrics PET trace 80 cyclotron (GE Healthcare, Sweden, Uppsala). The aqueous radioactive solution was transferred to an appropriate shielded hot cell (COMECER) using Helium pressure of 2 bars. Typical irradiation times were 60 min with a beam current of 40 µA, which yielded a [$^{18}$F]-fluoride amount of about 70 GBq at end of bombardment.

Automated Synthesis.

All loading operations were conducted under an ambient atmosphere.

A remote controlled GE TracerLab FX FN module was used for the automated radiolabelling experiments. Helium was used as a pressurizing gas during sample transfers. All the SEP-Paks cartridges were purchased from Waters Corporation. Prior to use, QMA-light Sep-Paks were flushed with 10 ml of ethanol, followed by 10 ml of 90 mg/ml potassium trifluoromethanesulfonate solution, and 10 ml of sterile water prior to use. Alumina N Sep-Paks were pre-conditioned with 10 ml of sterile water and C18 Sep-paks lights with ethanol (2 ml) and sterile water (10 ml). Preparative HPLC separations were all done on the GE Tracerlab FX FN module with a Gemini C18 5 µm 250×10 mm column (Phenomenex), isocratic elution: NH$_4$OAc 0.1M (pH 6)/MeCN 50/50 (v/v); flow rate: 4.7 ml/min; room temperature; UV detection λ=254 nm. The HPLC Analysis were performed on a Thermofisher UPLC Ultimate 3000 system equipped with a UV spectrophotometer and a Berthold LB509 radioactivity detector, column: Gemini C18 250×4.6 mm, 5 µm (Phenomenex), isocratic elution: NH$_4$OAc 0.1M (pH 6)/MeCN 50/50; flow rate: 1 ml/min; room temperature, UV detection λ=254 nm.

Scheme 4

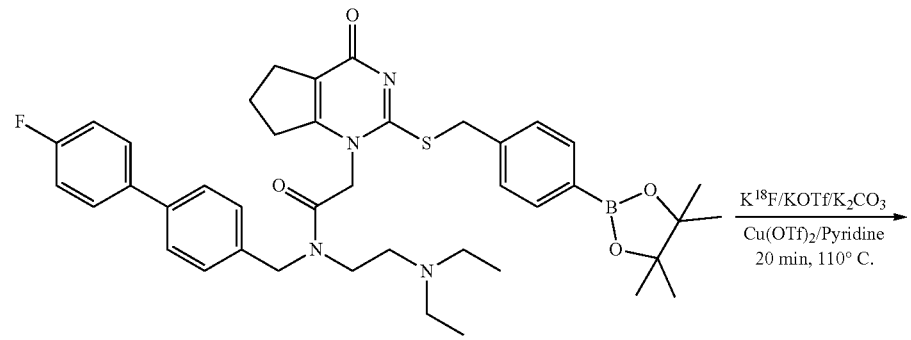

-continued

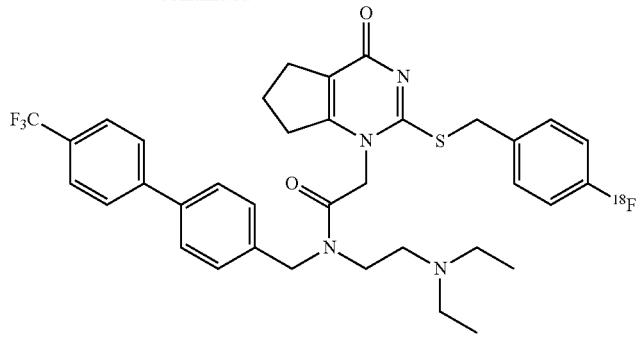

2.2. Synthesis of $K^{18}F$

The 1.5 ml bolus of [$^{18}$O]water containing 70 GBq of [$^{18}$F] Fluoride was delivered to the synthesis module and trapped in a QMA-light Sep-Pak cartridge to remove the excess of [$^{18}$O]water and others impurities. The activity was released from the cartridge into the reaction vessel by the aqueous solution of $KOTf/K_2CO_3$. The 1 ml of acetonitrile from V2 was poured into the reaction vessel and the resulting solution was dried by azeotropic distillation to provide $K^{18}F$. This step was achieved by heating the reaction vessel to 120° C. under vacuum during 6 min. Overall, around 70% of activity remained after this first step.

2.3. Automated Synthesis of [$^{18}$F]-Darapladib

During this second step of the automated program, the reactive mixture contained in vial 3 [precursor 9 (4 mg, 5 µmol, 0.005 M), $Cu(OTf)_2$ (9 mg, 25 µmol, 0.02 M), Pyridine (52 µl, 644 µmol, 0.62 M) in a solution of NMP and n-BuOH] was poured into the reaction vessel with the dried $K^{18}F$ by applying helium pressure. Before starting the radiolabelling of the precursor 9, vial 2 was opened to bring some air into the reaction vessel. After shutting the valve of vial 2, the mixture was then stirred for 20 min at 120° C. The reaction vessel was the cooled to 50° C. with compressed air cooling before adding 1.5 ml of HPLC eluent from V4. The solution was sucked into the HPLC vial. The reaction vessel was finally cleaned by adding another portion of 1.5 ml of HPLC eluent and immediately transferred into the HPLC vial. The whole volume contained in the HPLC vial was sent into the preparative HPLC. The [$^{18}$F]-Darapladib was collected into the dilution flask. At the end of the collection, the formulation step was started by passing through a Sep-Pak Plus C18 cartridge (Waters). The final activities were measured into a shielded glove box with dose calibrator SCIN-TIDOSE (Lemer Pax, Carquefou, France).

Figure 10:
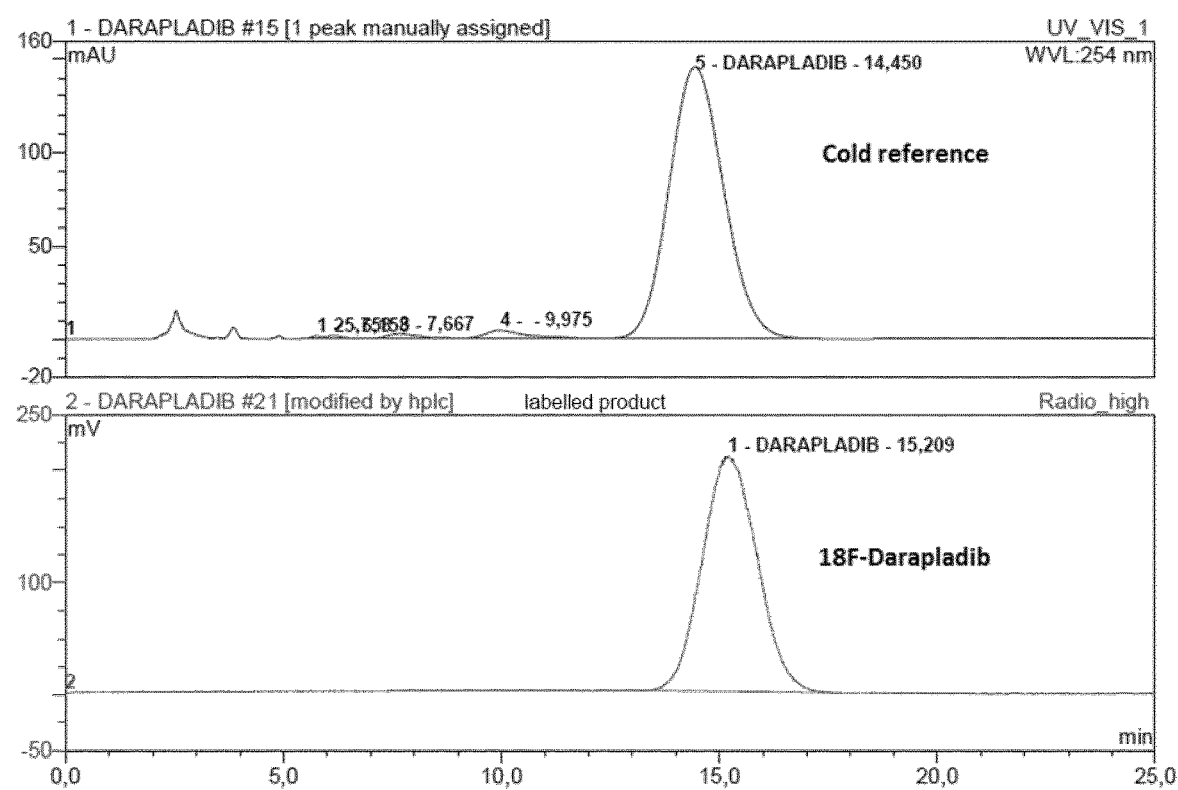
FIG. 10:
Cold reference (UV) and [18F]-Darapladib (Radio HPLC).

2.4. Quality Control of [$^{18}$F]-Darapladib (See FIG. 10)

Quality controls were carried out before administration of the tracers. The batches were expected to be clear, colorless and free of particulates. pH were measured using pH paper strips. The pH values were expected to range between 4.5 and 8.5 due to the mice injection specifications. The radiochemical purities (RCP) and the specific activities (SA) were measured with the analytical HPLC system.

Results

The radiochemical purities were 94.5±0.7% (n=9). The injected specific activities were 10.1±2.3 GBq/mol.

3. In Vitro and In Vivo Studies

3.1. General Materials and Methods

All reagents and solvent were purchased from commercial suppliers and used without further purification (Acros and Sigma-Aldrich).

In Vitro Studies.

The stabilities in PBS buffer were analyzed by analytical HPLC [Thermofisher UPLC Ultimate 3000 system equipped with a UV-Vis spectrophotometer with diode array detector; column: Gemini C18 250×4.6 mm, 5 µm (Phenomenex), isocratic elution: $NH_4OAc$ 0.1M (pH 6)/MeCN 50/50; flow rate: 1 ml/min; room temperature].

In Vivo Studies.

Apolipoprotein E-deficient mice (ApoE (−/−) or ApoE KO) and C57Bl6 mice were purchased from Charles River Laboratories (Saint-Germain-sur-L'Arbresles). All the animals were maintained at a constant temperature (24±1° C.) and a hygrometry between 55 to 65% under a 12 hour light/dark cycle, and permitted free access to food and water. Mice were handled and cared in accordance with the Guide for the Care and Use of Laboratory Animals (national Research Council, 1996), the European Council Directive 2010/63/EU and approved by the Ethics Committee no 114 for Animal Experimentation under the reference APAFIS #6271-201605021622180v2, under the supervision of authorized investigators.

PET Imaging Studies.

Animals were scanned on a small-animal multimodal scanner (Triumph II, PET/SPECT/CT, Trifoil Imaging, Chatsworth, Calif., USA) under anesthesia (isoflurane, 3% induction and 1.5% maintenance in air). Beforehand, mice were anesthetized with isoflurane (3%) and injected with the radiotracers in the caudal lateral vein using a 30-gauge catheter. [18F]FDG doses were supplied by GIP CYROI (Sainte-Clotilde, Reunion Island). The biodistribution studies were performed on a Gamma counter Wizard 2470 (Perkin Elmer, Groningen, The Netherlands).

Figure 11:
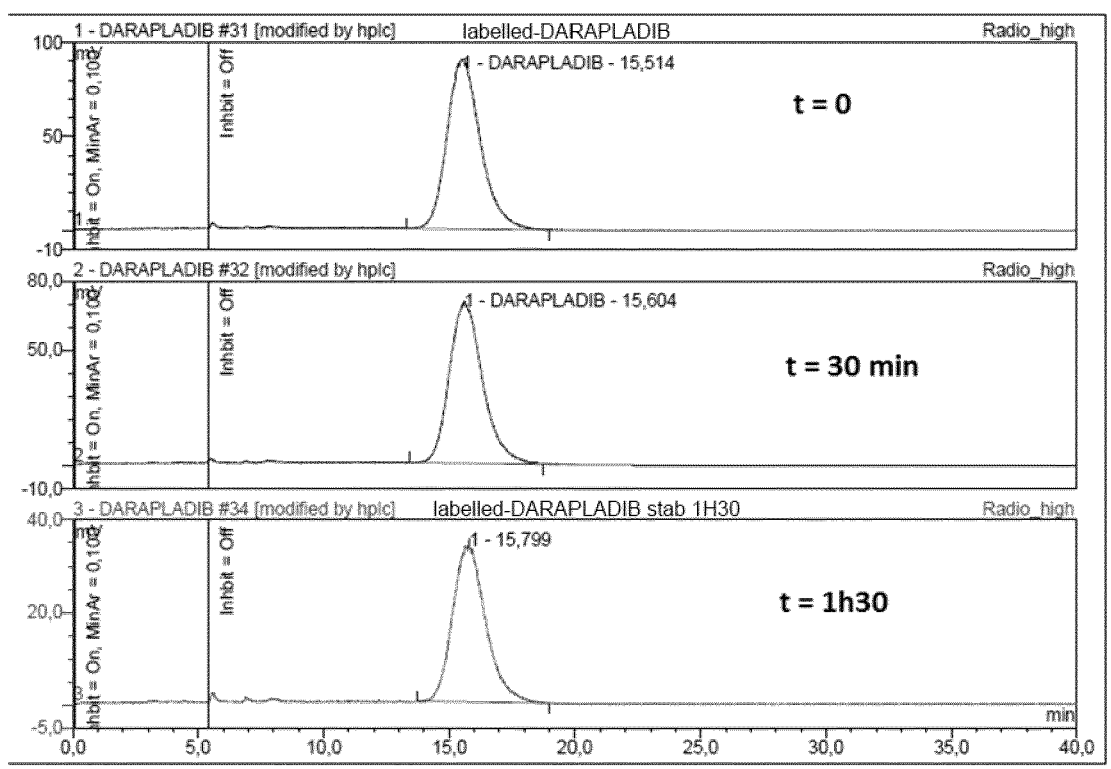
FIG. 11:
Stabilities in buffer of [18F]-Darapladib.

3.2. Stabilities in Buffer of [$^{18}$F]-Darapladib (See FIG. 11)

The stabilities of the labeled peptides in Phosphate Buffer Saline (PBS) 1× pH 7.0 were performed at different time points (0, 30 min and 1 h 30 min) post synthesis at a temperature of 37° C.

3.3. In Vivo Studies

3.3.1. Atherosclerosis Models Studies

Atherosclerosis Models.

Apolipoprotein E-deficient mice (ApoE (−/−) or ApoE KO) were chosen as models for atherosclerosis studies. Mice were bred in the animal facility until the age of 18-20 months for the study. 5 ApoE KO mice were used for each radiotracer. To compare with normal mice, 5 C57Bl6 mice were used for each radiotracer.

Pet Imaging.

Injected doses of radiotracers [$^{18}$F]FDG or [$^{18}$F]Darapladib were 15±5 MBq. The PET imaging distributions of mice were assessed at time intervals from 0 to 1 h post-injection with four images of 15 minutes each.

Biodistributions.

At the end of the PET imaging acquisitions, the animals were sacrificed by cardiac puncture. The heart and aorta were isolated, blood-flushed and placed under the multi-modal imager. A PET acquisition of 15 minutes was performed specifically on these tissues to measure the activity associated to the atherosclerosis plaques. At the end of this acquisition, all the organs were collected and placed into glass tubes for the γ-counter measurements.

3.3.2. Tumor Model Studies

Cell Culture

The tumor cell line B16 was purchased from Sigma (Saint-Quentin-Fallavier, France). This cell line was cultivated in RPMI1640 supplemented with 10% fetal calf serum, 2 mM glutamine, 100 units/ml streptomycin, 100 units/ml penicillin and 1.25 pug/ml fungizone. Cells were maintained in a 5% CO$_2$ humidified atmosphere at 37° C. Cell viability was over 90%, as determined by trypan-blue staining. Immediately before implantation in mice, cells were centrifuged and adjusted to a concentration of 25×10$^6$ cells per ml in PBS 1× for subcutaneous injection.

Tumor Models.

Six to eight weeks old mice C57Bl6 mice were used for implantation of B16 cells. A B16 tumor cell suspension containing 1×10$^6$ cells in a volume of 0.2 ml was injected subcutaneously into right flank using a 27-gauge needle. The experiments were performed when tumors were 150-250 mm$^3$ (tumor volume measurement was performed by digital caliper).

Pet Imaging.

Injected doses of radiotracers [$^{18}$F]FDG or [$^{18}$F]Darapladib were 15±5 MBq. The PET imaging distributions of mice were assessed at time intervals from 0 to 1 h post-injection with four images of 15 minutes each.

Example 2

Darapladib Synthesis is described in Example 1.

The same methodology was applied to the radiofluorination precursors synthesis. Darapladib groups 3 and 4 were synthesized as described before (Scheme 4).

Scheme 5. Four moieties of Darapladib involved in Lp-PLA$_2$ recognition.

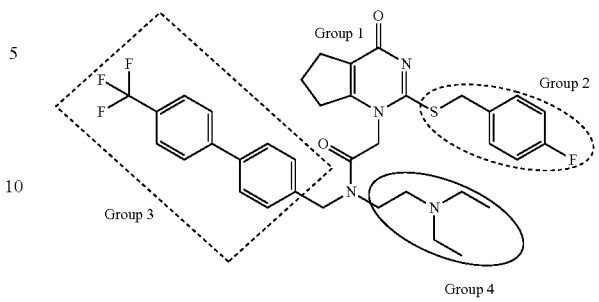

In order to produce the radiolabelling precursor, the present inventors have worked on the sulfur alkylating agent that would provide $^{18}$F-labelling via an arylboronate moiety (see Scheme 1 of Example 1).

4-bromobenzaldehyde was reduced to the corresponding alcohol in 91% yield. In a palladium catalyzed coupling, the boronate moiety was inserted in 91% followed by bromination via CBr$_4$ (94%). As shown in Scheme 2 of Example 1, radiolabelling precursors 9 have been synthesized since the present inventors previously showed that the corresponding fluorine molecule (Darapladib) was able to reduce drastically Lp-PLA$_2$ activity (IC$_{50}$=0.1 nM).

Compound 4 was synthesized as described previously and engaged in a substitution with alkylating agent 3 to afford the thiouracile derivative 5 in 98% yield. Alkylation with tert-butylbromoacetate, yielded the desired precursor 6 (26%) which was hydrolyzed in TFA to afford acid 7. Peptide coupling of 8 and 7 allowed to obtain Darapladib-arylboronate radiolabelling precursor 9 in 65% yield.

To produce radiolabelled inhibitors 30% of n-BuOH as a co-solvent in NMP was used (Scheme 6).

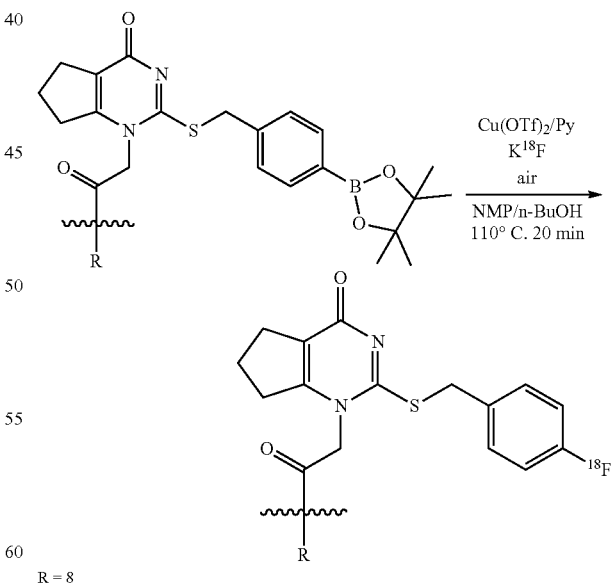

As shown in Table 2, it is possible to obtain and $^{18}$F-Darapladib in much better yields than as described in the prior art (Sanford et al. and Zichler et al.—Johannes Zischler, Niklas Kolks, Daniel Modemann, Bernd Neumaier, Boris D. Zlatopolskiy. Alcohol-enhanced Cu-mediated radiofluorination, Chemistry—A European Journal Volume 23, Issue 14 Mar. 8, 2017 Pages 3251-3256)

TABLE 2

Enhanced copper-mediated radiofluorination of 9.

| Entry | Solvents | Activity (MBq)[a] | RCY[b] |
|---|---|---|---|
| 1 | DMF | 257 | <1% |
| 2 | NMP | 379 | 1% |
| 3 | NMP/n-BuOH | 2310 | 6% |
| 4 | NMP/n-BuOH | 1979 | 5% |

[a]Before formulating process
[b]Activity corrected

Elution of $^{18}$F from QMA cartridge was performed using a KOTf/K$_2$CO$_3$ aqueous solution (5 mg/50 µg). The eluted fluorine was azeotropically dried twice (60° C. then 120° C.) since copper-mediated labelling is highly water sensitive (as described in Sanford et al). Reactions were carried out at 110° C. under pressure for 20 min. Since copper complex needs to be oxidized, air was injected 4 times during reaction course. The reaction mixture is then loaded on HPLC to be purified then formulated in water (5% EtOH content). As previously indicated, radiofluorination in DMF yielded the desired radiotracer in a very low yield (entry 1) and NMP did not show any significant improvement (entry 2), both methods leading to 1% or less recoveries. Working in a mixture of NMP/n-BuOH (660 µL/330 µL) allowed to significantly increase $^{18}$F-Darapladib radiofluorination up to 6%. Activities recovered were sufficient to perform PET studies.

Radiolabelled Darapladib was injected in caudal vein in two mice models. As a comparison, $^{18}$FDG was also injected as the reference in inflammation for PET imaging. The present inventors first worked on an tumor-induced inflammatory model to test the specificity of $^{18}$F-Darapladib. Melanoma B16 tumors were induced in C57Bl6 mice that were intravenously injected via tail. As shown in FIG. 1, $^{18}$FDG accumulated markedly in the tumor whereas $^{18}$F-Darapladib did not show any detectable signal.

Figure 2:
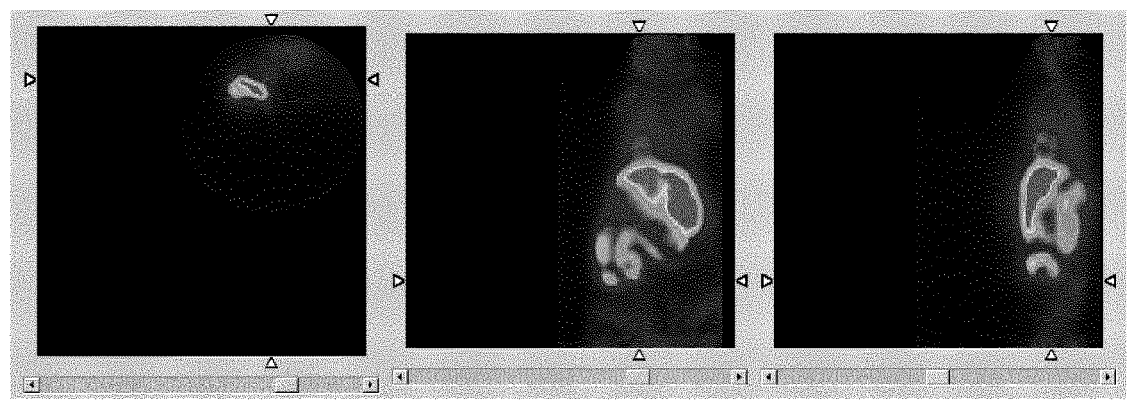
FIG. 2:
Injection of [18F]Darapladib in ApoE KO mice (12 MBq—Whole body PET imaging).
Accumulation in the heart, liver, kidneys, bladder and intestines. From left to right, transverse, coronal and sagittal views.
Figure 3:
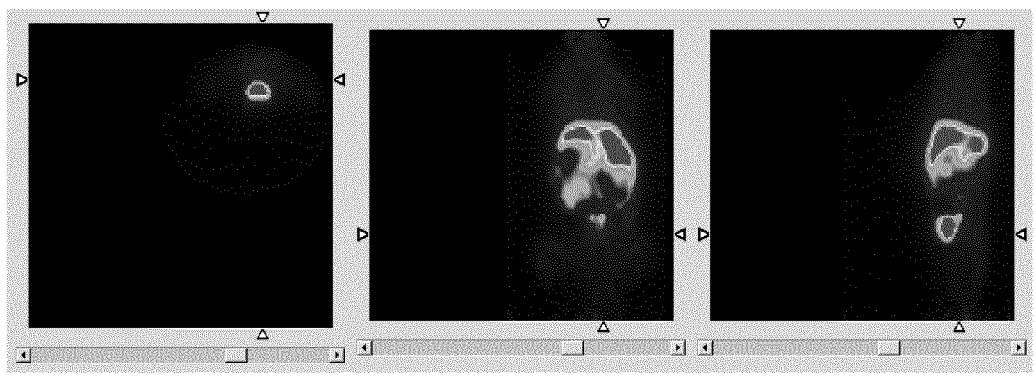
FIG. 3:
Injection of [18F]Darapladib in C57Bl6 (14 MBq).
Accumulation in the heart, liver, kidneys, bladder and intestines. From left to right, transverse, coronal and sagittal views.

The present inventors worked on an atherosclerosis mice model (knock-out ApoE mice) in order to compare both $^{18}$FDG and $^{18}$F-Darapladib abilities to target atheroma plaques and fatty streaks. As for the inflammatory model, mice were injected via tail and imaged for one hour. However, as shown on FIG. 2, whole body imaging did not allow to see any accumulation in the aorta compared to control (FIG. 3).

However, Darapladib in vivo metabolism was studied and accumulation was observed in heart, liver, pancreas, spleen, kidneys, bladder and intestines. Liver accumulation was expected since it is the path to lipoproteins metabolism where LDL and HDL are migrating. The others organs radiolabelled are due to Darapladib coverage and elimination. In comparison, $^{18}$FDG accumulated in brain, heart as they are the main glucose organs consumers. Kidneys and bladder were also labeled and follow glucose elimination processes. No differences were observed either in KO ApoE and C57Bl6 mice.

In order to target blood vessels more precisely, it was sampled both the aorta and heart and performed a 15 min PET acquisition (FIGS. 4, 5, 7A and 7B).

Figure 4:
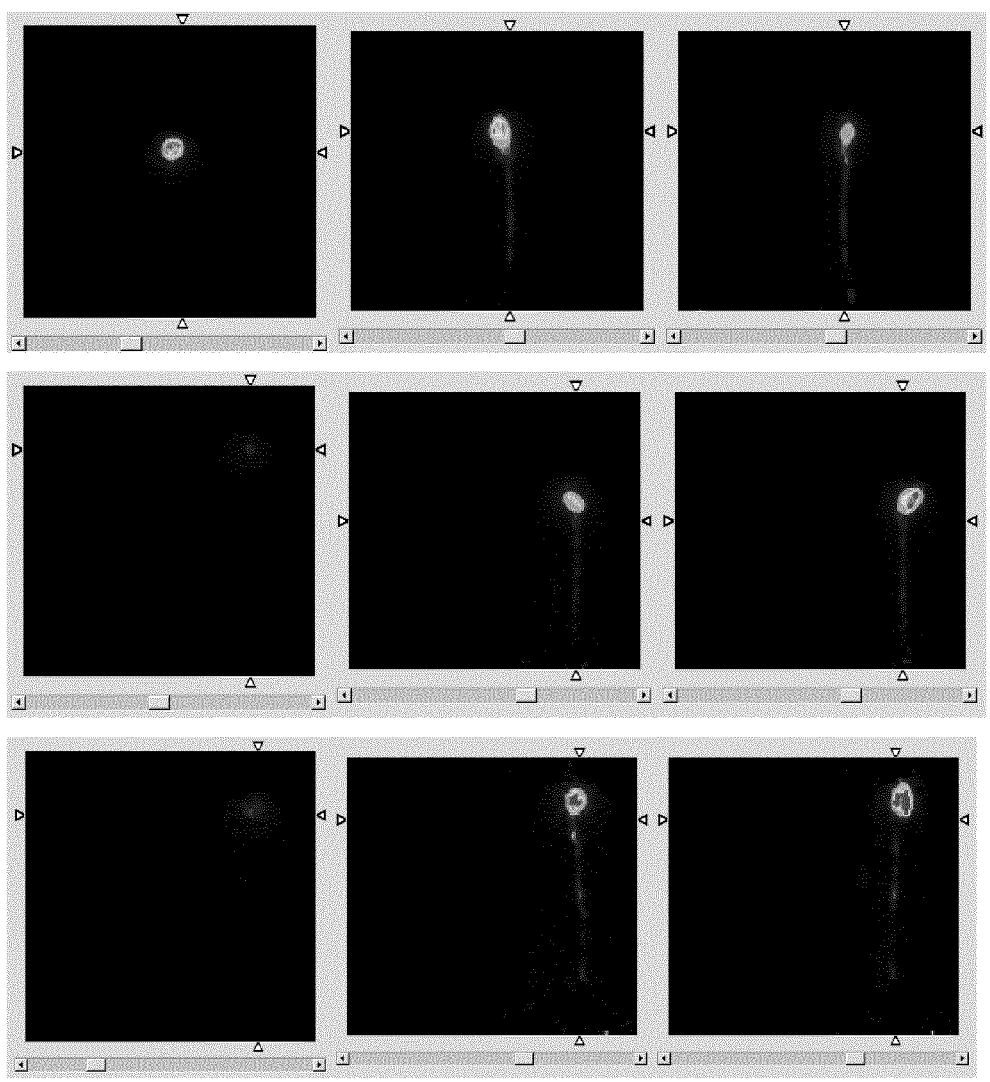
FIG. 4:
Injection of [18F]Darapladib in ApoE KO mice (17 MBq) (ex vivo—after dissection of the heart and aorta of the mice).
Accumulation in the heart (presence of blood through the coronary arteries).
Accumulation in aorta, in particular in aortic plaques, (no atheroma plaques).
From left to right, transverse, coronal and sagittal views.
Figure 9:
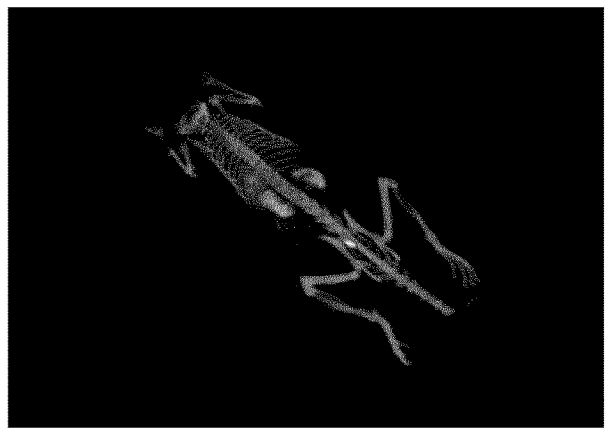
FIG. 9:
Injection of A4 compound in mice.
Accumulation in the liver, kidneys and bladder.

As shown in FIGS. 7A and 7B, no accumulation was observed for both models (control and ApoE KO) using $^{18}$FDG either in the aorta or in the arch. However as depicted in FIGS. 4 and 5, we can see that the aortic arch is highly radiolabelled with $^{18}$F-Darapladib as compared to control mice. We can also observe an accumulation within the aorta itself. Organs were sampled to perform biodistribution studies shown in FIG. 8.

In order to support atheroma plaques and fatty streaks accumulation in KO ApoE mice aortas, we dissected aortas ex-vivo. As depicted in FIG. 12B, aortas in KO ApoE mice showed a strong presence of atheroma plaques that correlates to $^{18}$F-Darapladib accumulation.

Example 3 (Synthesis of Darapladib Precursor)

Experimental Section

To synthesize a Darapladib precursor, it is important to find a suitable strategy to $^{18}$F-label arenes. Besides the gaseous [$^{18}$F]F$_2$ that provides low specific activity (SA) radiotracers, production of an aqueous solution of fluorine-18 can facilitate the acquisition of high SA compounds.

SNar reactions are the leading path to the formation of $^{18}$F-labeled aromatics. There are two main strategies available to perform radiofluorination of arenes that do not need electrophilic $^{18}$F sources or strong electron withdrawing groups. The first involves the radiofluorination of strong electrophiles in the mean of iodonium ylides or diaryliodonium salts. However, with electron neutral compounds those reactions require high temperature and offer low radiochemical yields (RCY). To address those limitations, a second strategy was initiated by Gouverneur et al[9]. This route targeted direct nucleophilic [$^{18}$F]-fluorination of a wide range of aryl boronate esters with [$^{18}$F]KF/K2.2.2 mediated by the commercially available copper complex [Cu(OTf)$_2$(Py)$_4$]. Sanford et al. proposed shortly after a new alternative that directly forms in situ the copper complex[10]. This method allows more constant yield and radiofluorination of both boronates and boronic acids derivatives.

We report herein the synthesis of $^{18}$F-radiolabeled Darapladib via alcohol enhanced Cu-mediated radiofluorination in order to target vulnerable atheroma plaques (Scheme 7). In vitro and in vivo datas of [$^{18}$F]-Darapladib are shown herein.

Scheme 7. Copper-mediated radiofluorination of aryl boronates

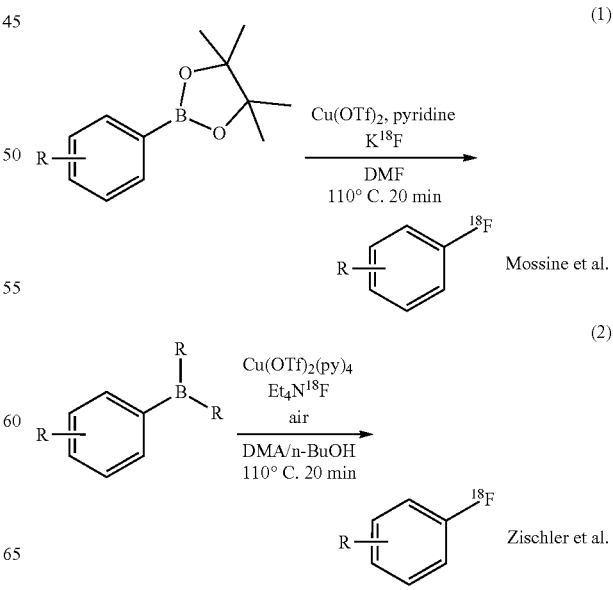

-continued

R = H, 2R = pinacolyl

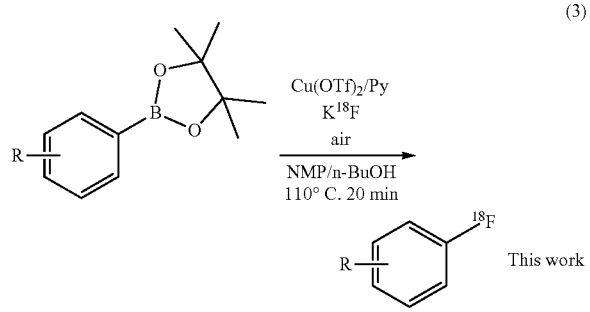

(3)

This work

Experimental Procedures

Material and Methods.

Darapladib and its radiolabelling precursor were synthesized by improving procedures adapted from the literature. In order to perform PET imaging, a 10 month-ApoE knockout mouse model containing atheromatous plaques was used. $^{18}$F-Darapladib and [18F]-deoxyglucose (used as positive control for detection of metabolically active cells) were injected to both ApoE KO and control C57Bl/6 mice. Animals were imaged for one hour and then sacrificed. The aorta and heart were sampled and imaged ex vivo for 15 min. Organs were also sampled to perform biodistribution studies. Imaging was also performed on human carotid endarterectomy samples ex vivo by incubation with both radiotracers separately.

Results and Discussions.

Cold reference 19F-Darapladib was obtained with a 34% global wield on 6 steps while its precursor arylboronate-Darapladib was synthesized with a 4% yield on 10 steps. Radiolabelling of [$^{18}$F[-Darapladib was automated with a 6% corrected radiochemical yield and a radiochemical purity over 99%. Total body mouse imaging did not allow to show intravascular accumulation. However, Darapladib accumulated in liver, pancreas, spleen, kidneys, bladder and intestines. More importantly, aorta and heart ex vivo imaging on ApoE KO mice allowed us to see accumulation in the aortic arch and in aortic plaques. WT mice did not show any labelling. [18F]-FDG, on both control and ApoE KO mice did not accumulate within the aorta. Incubation of human carotids ex vivo showed a strong accumulation in the lipid core of the plaques.

A radiolabelling precursor that allowed to obtain [18F]-Darapladib was synthesized. Imaging studies showed promising results in a murine atherosclerosis model but also ex vivo in human carotid samples.

Example 4 (General Synthesis of Darapladib and Analogs)

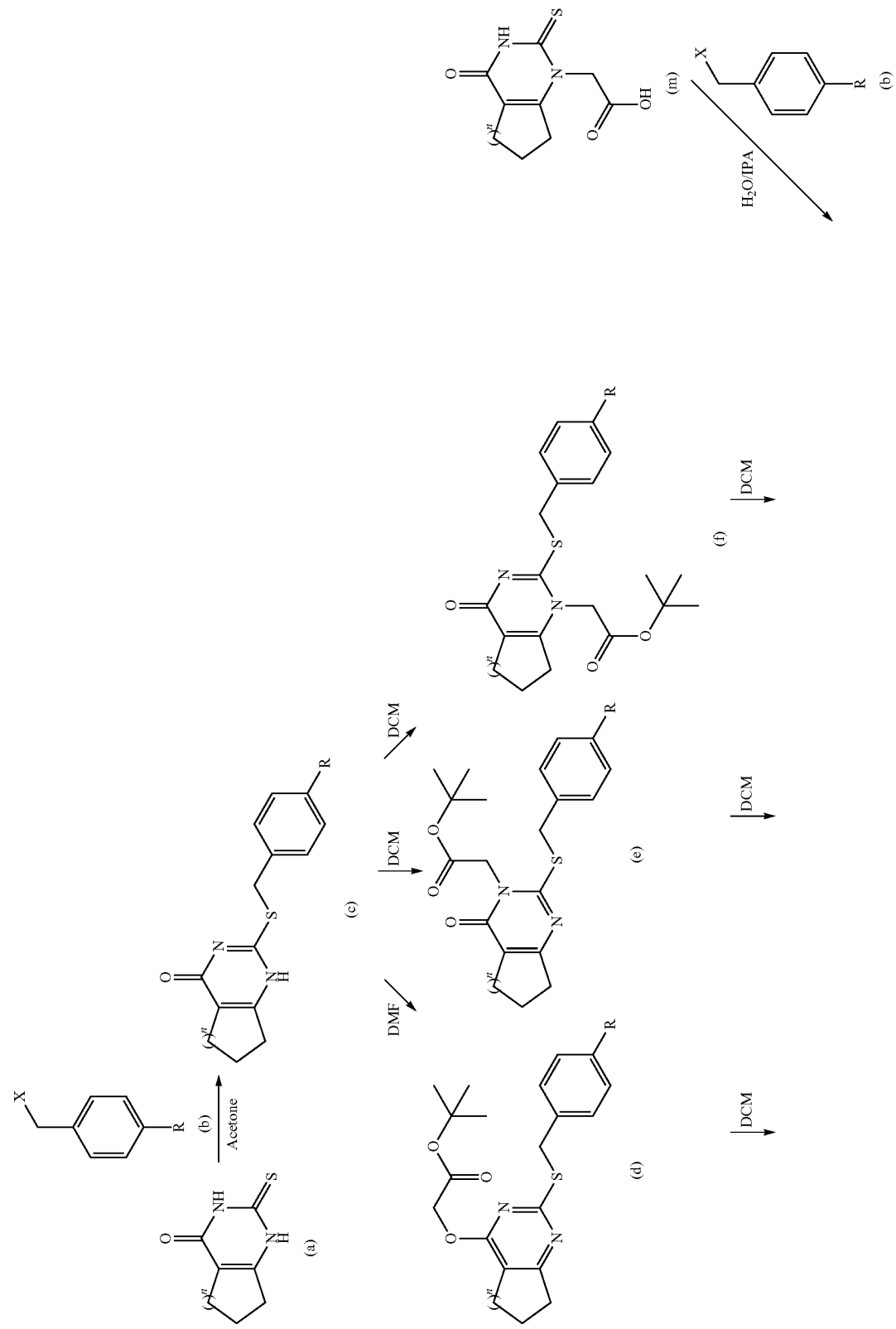

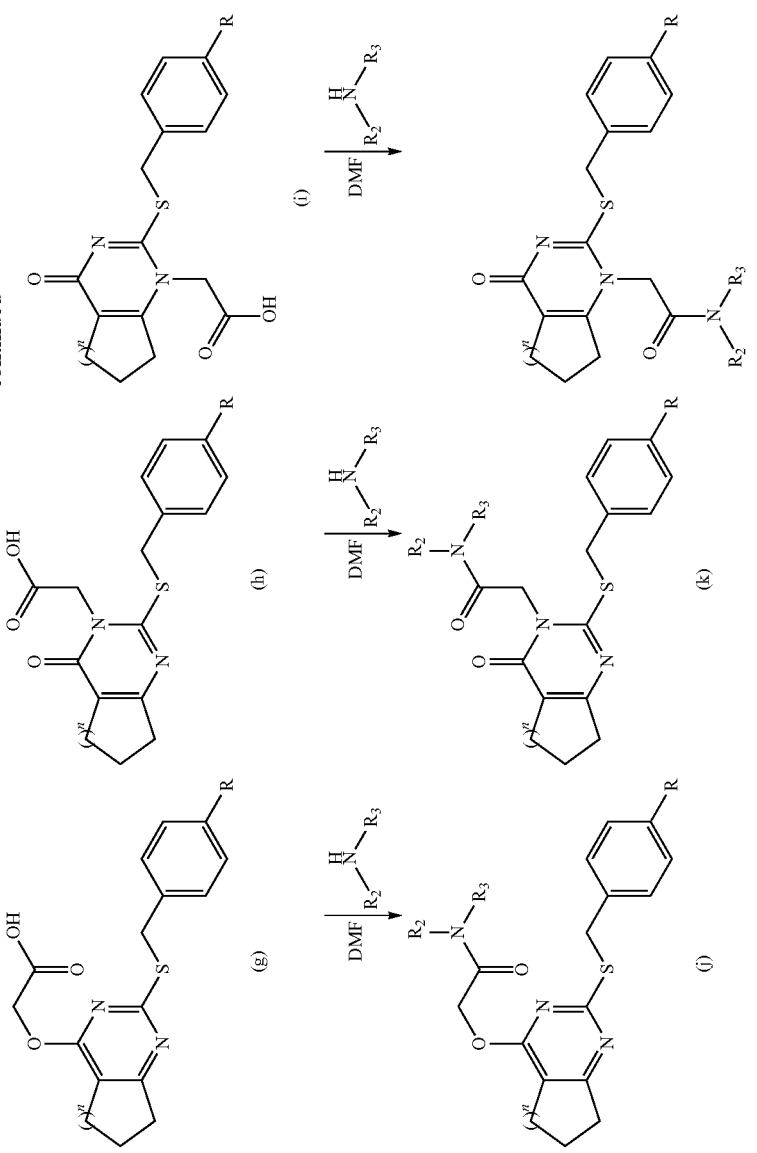

Compound (a) can be obtained by reported procedures (Cardwell, K. S.; Crawford, C. F.; Davies, S. H.; Wade, C. E. Novel processes. WO Patent 146,494, 2011; *Bioorg Med Chem Lett*. 2018 Feb. 15; 28(4):787-792. doi: 10.1016/j.bmcl.2017.12.052). Compound (b) R group can represent a precursor derivative such as boron esters or iodonium ylides described in the scheme 10 below. For cold references, R represents a 19-fluorine atom. X is representative of an halogen or a leaving group such as CF3, I, Br, Cl, OTs, OTf or Oms. Compound (b) is synthesized as previously described (Rotstein B. et al. Nat Commun. 2014 Jul. 9; 5:4365. doi: 10.1038/ncomms5365; *Chem Commun (Camb)*. 2016 Jun. 28; 52(54):8361-4. doi: 10.1039/c6cc03295 h). Alkylation of compound (a) to form compound (c) is performed in acetone. Regioselective alkylation of (c) can be performed in DMF to obtained compound (f). N1 or N3 alkylation of compound (c) to obtain compounds (e) and (f) is performed in DCM. Alkylating agent used to obtain compounds (d), (e) or (f) is tBu-4-bromoacetate in the presence of a hindered base such as DiPEA. Such compounds can be obtained by reacting Removal of the tert-butyl esters is performed in DCM with an excess of an acid such as TFA to obtain compounds (g), (h) and (i). Alternatively, compound (i) can be obtained from compound (m) in a mixture of polar protic solvents such as $H_2O$/IPA with an inorganic base such as $K_2CO_3$. If more reactive compounds derived from (g), (h) and (i) are desired, they can be reacted with TSTU in the presence of a base such as DiPEA to produce N-succinimidyl prosthetic groups. Final compounds (j), (k) and (l) can be obtained from a peptide coupling in DMF using uronium coupling agents such as COMU. The secondary amine used can be obtained with various alkylation $R_2$ or $R_3$ from reported procedures (*Bioorg Med Chem Lett*. 2018 Feb. 15; 28(4):787-792. doi: 10.1016/j.bmcl.2017.12.052; *Bioorg Med Chem Lett*. 2013 Feb. 1; 23(3):839-43. doi: 10.1016/j.bmcl.2012.11.061). Scheme 9 shows the synthesis of amines of formula $R_2$—NH—$R_3$. $R_2$ and $R_3$ are described in the listing below. Alternatively, the amine used can be 4-aminobutyl 4-methylbenzenesulfonate obtained from the corresponding aminoalcohol in the presence of TsCl.

A N-succinimidyl group has the following formula:

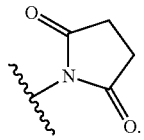 [SMILES: *N1C(=O)CCC1=O]

In scheme 8, $R_2$ and $R_3$ may represent one of the following groups:

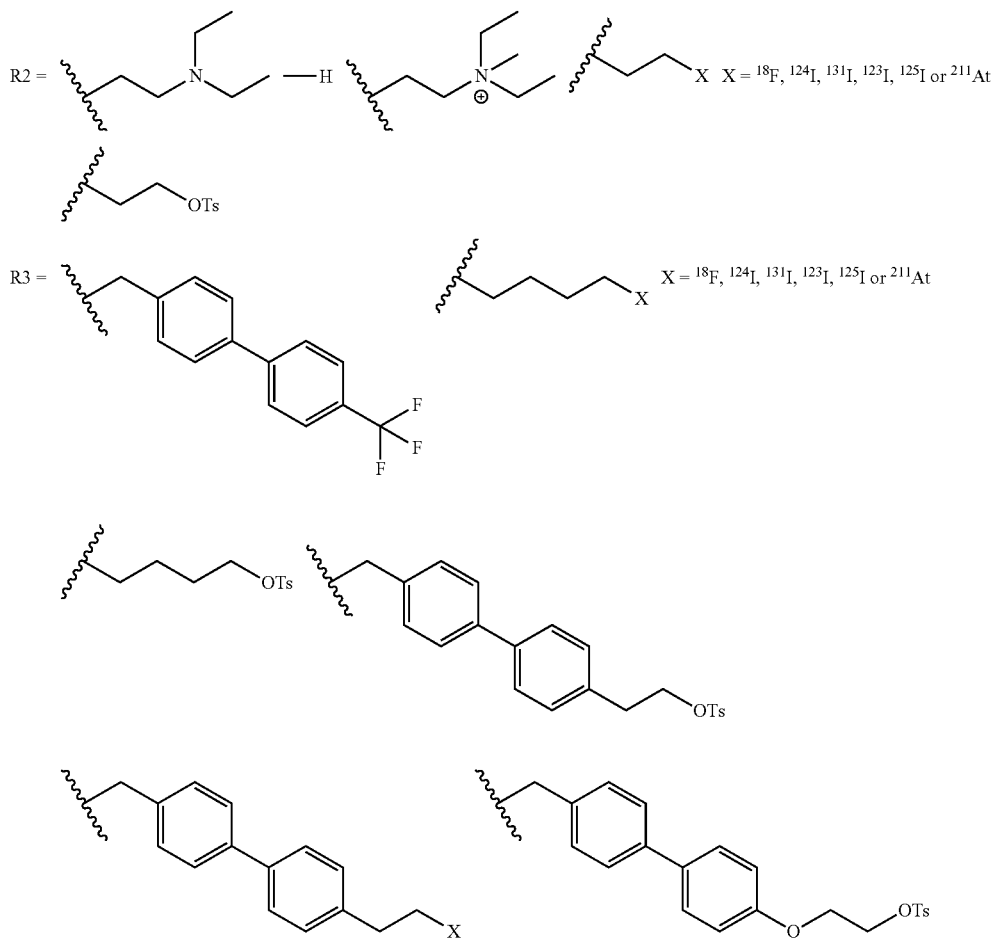

Listing of $R_2$ and $R_3$.

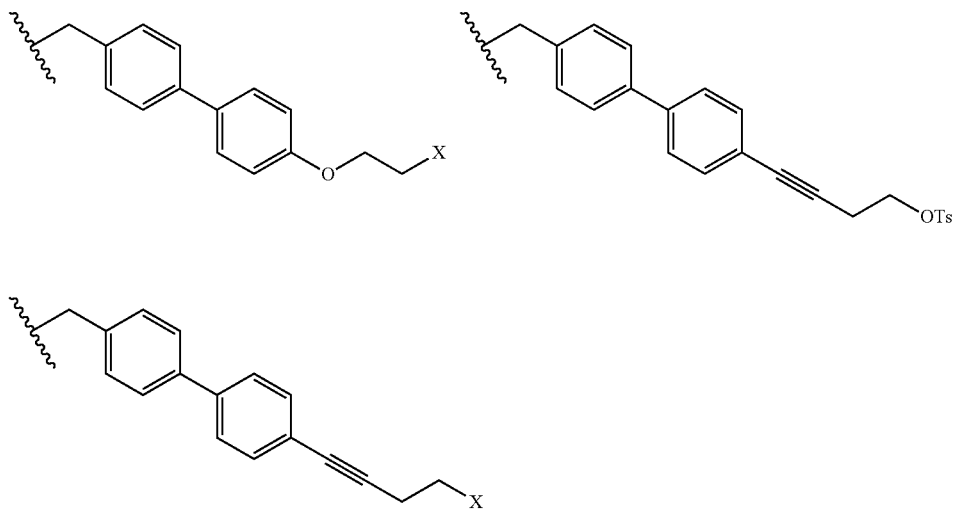
R2 and R3 can optionally form a cycle (see compounds A48 and A49 in table 1). A peptide coupling from the corresponding piperazine enables to obtain compounds A48 and A49.
Scheme 9. Synthesis of radio-labeling precursors
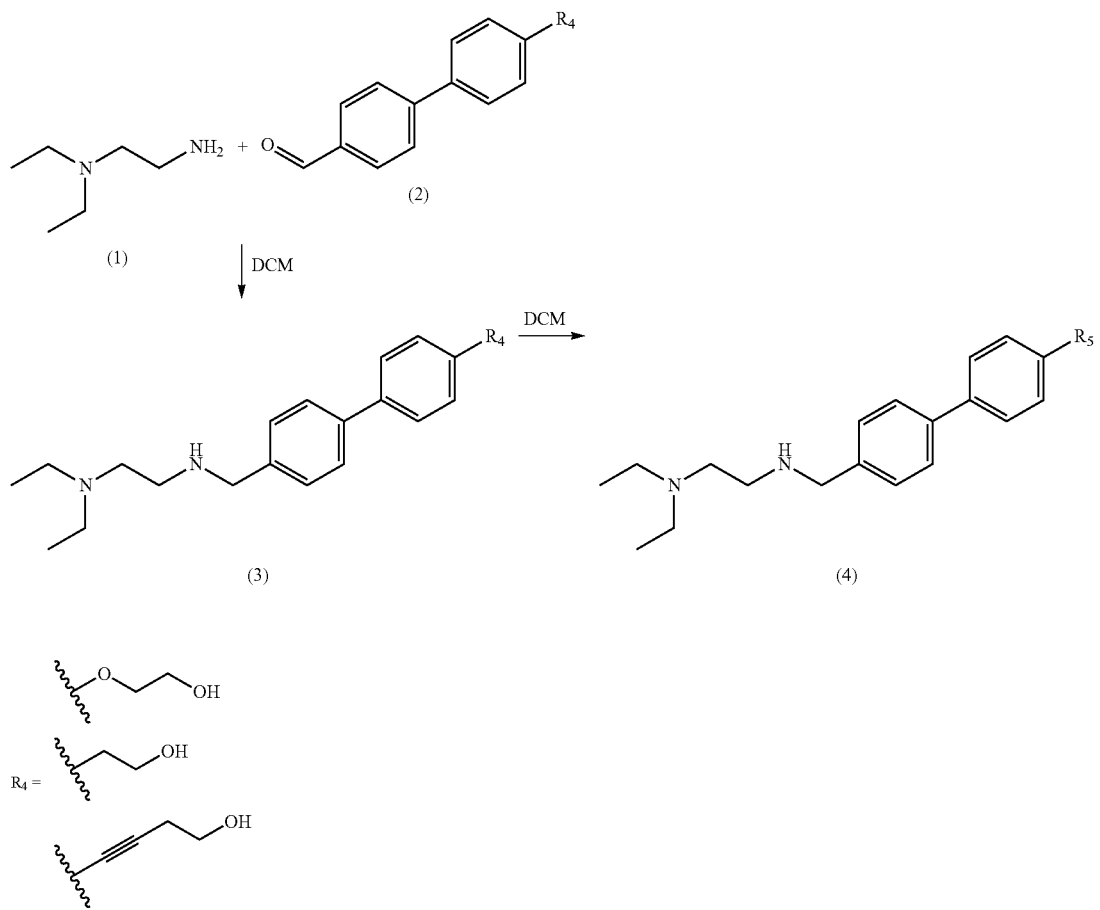

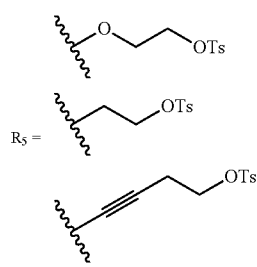

Commercially available compound (1) and corresponding aldehyde (2) (which can be modified by reported procedures from halides or corresponding alcohols) are reacted in a reductive amination in DCM in the presence of a reducing reagent such as NaBH(OAc)$_3$ to produce compounds (3). The corresponding amino-alcohol obtained is reacted with TsCl in DCM to produce the corresponding radio-labeling precursors (4).

Commercially available compound (a) can be reacted in DMSO in a Pd catalysed coupling to form boronic ester (b) or in THF through organolithium to obtain corresponding boronic acids. Alternatively, compound (a) can be treated with AcOH to form corresponding diacetoxyiodoarenes (c) that can be easily converted in corresponding iodonium salts (e) in AcOH in the presence of a catalyst such as sulfuric acid. Compound (c) can also be converted to the corresponding aryl ylide (d) in EtOH in the presence of Na$_2$CO$_3$.

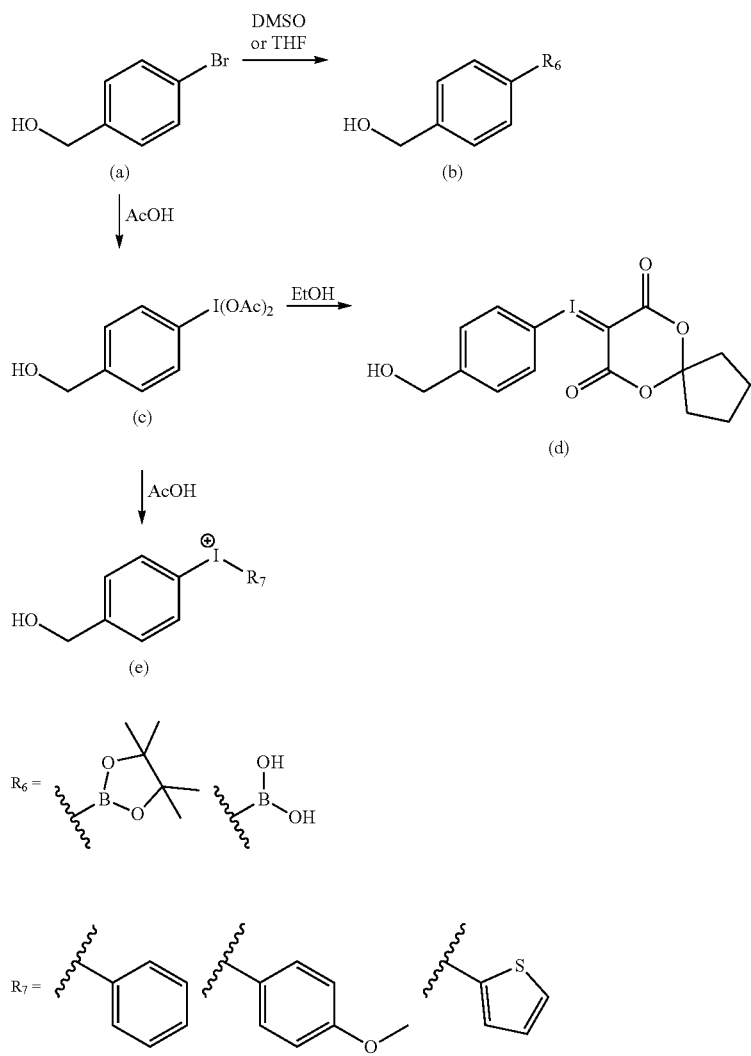

Example 5 (In Vivo and Ex Vivo Studies—[¹⁸F]N1-FGU Herein Referred as Compound A4)

[¹⁸F]N1-FGU herein referred as compound A4 has been synthesized according to the general synthesis method as described on pages 51-52.

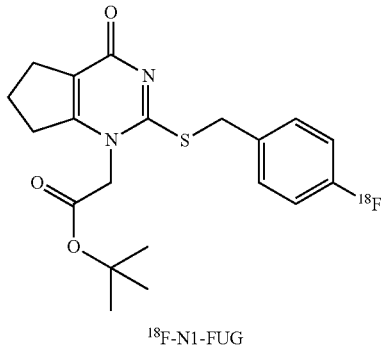 [SMILES: CC(C)(C)OC(=O)Cn1c(SCc2ccc([18F])cc2)nc(=O)c2c1CCC2]

¹⁸F-N1-FUG

As shown in FIGS. 14a and 14b, the whole body biodistribution of [¹⁸F]N1-FGU after 15 minutes intravenous injection of 20 MBq of [¹⁸F]N1-FGU is similar to that of [¹⁸F]darapladib, i.e. showing an accumulation in the liver and intestine. No major difference could be observed between non atherosclerotic C57BL/6 mice and atherosclerotic ApoE KO mice.

As shown in FIGS. 15a and 15b, the ex vivo imaging of the block heart/aorta shows an accumulation of [¹⁸F]N1-FGU in the heart and specifically in atheromatous lesions present in the ApoE KO mice in comparison to C57BL/6 mice. The corresponding macroscopic images on black wax background of the corresponding aortas after dissection and exposure of the endothelial face revealing the white atheromatous plaques in ApoE KO mice (see FIG. 15b).

As shown in FIGS. 16a and 16b, the ex vivo incubation of human carotid endarterectomy samples with [¹⁸F]FDG and [¹⁸F]N1-FGU led to strong positive signals in the different segments carotid samples (containing intraplaque haemorrhage or in adjacent non complicated areas) with the [¹⁸F]N1-FGU in comparison to [¹⁸F]FDG. The activity used was 30 MBq for each radiotracer. FIGS. 16a and 16b also show samples from the same patient symmetrically dissected for separated incubations with [¹⁸F]FDG and [¹⁸F]N1-FGU.

Example 6 (Ex Vivo Studies Herein Referred as Compound A12)

¹⁸F—O-FGU herein referred as compound A12 has been synthesized according to the general synthesis method as described on pages 51-52.

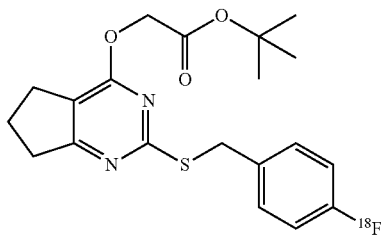

¹⁸F-O-FGU

As shown in FIGS. 17a and 17b, the ex vivo imaging of the block heart/aorta show a non-specific accumulation of ¹⁸F—O-FGU in the heart and along the aorta of both non atheromatous C57BL/6 (16 MBq) and ApoE KO (22 MBq) mice. Whole body imaging shows a similar distribution in C57BL/6 and ApoE KO mice, with an important accumulation in the bladder, intestine and kidneys.

REFERENCES (1) Koeppe R A. et al. Alzheimers Dement. 2010, 6(3), 221-229.
(2) Knuuti J. et al. Circulation. 2010, 122, 603-613.
(3) Le Bars D. Journal of Fluorine Chemistry. 2006, 127, 1488-1493.
(4) Barrio J R. et al. Nucl. Med. Biol. 1996, 3, 189-199.
(5) Pike V W. et al. Eur. J. Org. Chem. 2008, 2008(17), 2853-2873.
(6) Pike V W. et al. Chem Comm. 2013, 49(21), 2151-2153.
(7) Rotstein B H. et al. Nat. Commun. 2014, 5, 4365-4371.
(8) Pike V W. et al. Chem Comm. 2013, 49(21), 2151-2153.
(9) Gouverneur V. et al. Angew. Chem. Int. Ed. 2014, 53, 1-6.
(10) Sanford M S. et al. Org. Lett. 2015, 17(23), 5780-5783.
(11) William A. et al. Methodist Debakey Cardiovasc J. 2014, 10(3), 139-145.
(12) Cai A. et al. Disease Markers, 2013, 34, 323-331.
(13) Blackie J. A. et al. Bioorg. Med. Chem. Lett. 2003, 13, 1067-1070
(14) Stability Investigators. N. Engl. J. Med. 2014, 370(18), 1702-1711.

The invention claimed is:

1. A compound of formula:

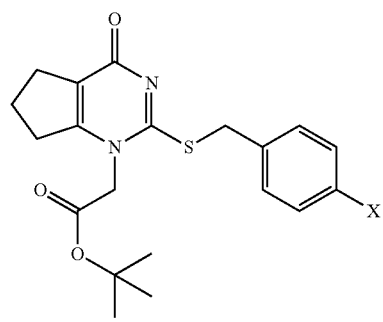

wherein X is —¹⁸F or

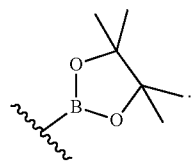 [SMILES: *B1OC(C)(C)C(C)(C)O1]

* * * * *